(12) United States Patent
Curran et al.

(10) Patent No.: US 9,314,381 B2
(45) Date of Patent: Apr. 19, 2016

(54) CAPACITIVE WETNESS SENSOR AND METHOD FOR MANUFACTURING THE SAME

(75) Inventors: Peter Curran, Oatley (AU); David Albert Barda, Rose Bay (AU); Don Black, Albert Park (AU); Bradley John Phillips, Glen Iris (AU); Peter Kotlarski, Glen Waverley (AU); Juuso Tuomas Olkkonen, Espoo (FI); Tomi Juha Petteri Mattila, Espoo (FI)

(73) Assignee: Fred Bergman Healthcare Pty. Ltd., North Sydney (AU)

( * ) Notice: Subject to any disclaimer, the term of this patent is extended or adjusted under 35 U.S.C. 154(b) by 82 days.

(21) Appl. No.: 14/236,255

(22) PCT Filed: Jul. 31, 2012

(86) PCT No.: PCT/AU2012/000900
§ 371 (c)(1),
(2), (4) Date: Apr. 24, 2014

(87) PCT Pub. No.: WO2013/016765
PCT Pub. Date: Feb. 7, 2013

(65) Prior Publication Data
US 2014/0296808 A1    Oct. 2, 2014

Related U.S. Application Data

(60) Provisional application No. 61/513,734, filed on Aug. 1, 2011.

(51) Int. Cl.
*G08B 21/00*    (2006.01)
*A61F 13/42*    (2006.01)
(Continued)

(52) U.S. Cl.
CPC ........... *A61F 13/42* (2013.01); *A61F 13/15699* (2013.01); *A61F 13/2051* (2013.01); *G01N 27/225* (2013.01)

(58) Field of Classification Search
CPC .... A61F 13/42; A61F 13/2051; G01N 27/225
USPC ...................... 340/604, 605, 573.5; 604/361; 200/61.04
See application file for complete search history.

(56) References Cited

U.S. PATENT DOCUMENTS 5,291,181 A * 3/1994 DePonte .................... 340/573.6
5,790,036 A    8/1998 Fisher et al.
(Continued)

FOREIGN PATENT DOCUMENTS

WO    9933037 A1    7/1999
WO    02052302 A2    7/2002
(Continued)

OTHER PUBLICATIONS

International Search Report dated, Aug. 29, 2012.
(Continued)

*Primary Examiner* — John A Tweel, Jr.
(74) *Attorney, Agent, or Firm* — Hansen IP Law PLLC

(57) ABSTRACT

A sensor device for sensing wetness in an absorbent article worn by a subject includes one or more sensing elements; and a coupling for communicating sensor signals between the one or more sensing elements and a receiver. A change in environmental parameter causes a change in electrical behavior of at least one of the sensing elements, which behavior can be analyzed to determine occurrence of a wetness event in the absorbent article. The changes in electrical behavior are communicated in the sensor signals to the receiver. The analysis may be by the receiver or a processor in communication with the receiver. Ideally, the sensing elements include capacitive elements and preferably, resonance circuits.

52 Claims, 11 Drawing Sheets

(51) Int. Cl.
  *G01N 27/22* (2006.01)
  *A61F 13/20* (2006.01)
  *A61F 13/15* (2006.01)

(56) References Cited

U.S. PATENT DOCUMENTS

| | | | |
|---|---|---|---|
| 6,987,232 B2 * | 1/2006 | Smith | H01H 3/142 |
| | | | 340/573.5 |
| 7,394,391 B2 * | 7/2008 | Long | A61F 13/42 |
| | | | 340/604 |
| 2002/0070868 A1 | 6/2002 | Jeutter et al. | |
| 2004/0036484 A1 | 2/2004 | Tamai | |
| 2004/0064114 A1 | 4/2004 | David | |
| 2004/0207530 A1 | 10/2004 | Nielsen | |
| 2010/0241094 A1 * | 9/2010 | Sherron | A61F 13/42 |
| | | | 604/361 |

FOREIGN PATENT DOCUMENTS

| | | |
|---|---|---|
| WO | 2007069945 A1 | 6/2007 |
| WO | 2010123425 A1 | 10/2010 |

OTHER PUBLICATIONS

Extended European Search Report for European Patent Application No. 12 820 230.6 dated Jan. 5, 2015.

* cited by examiner

CAPACITIVE WETNESS SENSOR AND METHOD FOR MANUFACTURING THE SAME

FIELD OF THE INVENTION

The present invention relates to sensing wetness. It relates particularly but not exclusively to a sensor and sensor arrangement and related components of a system for sensing wetness events such as urinary and faecal events as occur from time to time in a pad or diaper or similar absorbent article worn by a subject who may experience the condition of incontinence. The invention also relates to a system for coupling such sensors to a receiver and to methods for manufacturing sensors and/or absorbent articles incorporating sensors.

BACKGROUND TO THE INVENTION

Incontinence is a condition in which there is an uncontrolled release of discharges or evacuations. Urinary incontinence refers to loss of bladder control resulting in involuntary or uncontrolled urination. Other forms of incontinence include faecal or bowel incontinence.

Incontinence is a normal condition of infants and becomes less normal as the child ages. For infants an understanding of the subject's incontinence events and patterns of incontinence can assist in determining when to start training and monitoring the infant for self-awareness and self-management of their continence.

For adults there is a range of recognised forms of incontinence including stress/effort incontinence, urge incontinence, overflow incontinence, dribble incontinence, functional incontinence and the like. Treatment options include behaviour management, medication and surgery. Treatment options can be improved by having a good understanding of the patient's incontinence events and patterns of incontinence; this can be achieved by charting a patient's physiological control of their bladder or bowel over a period of time. However, in circumstances where treatment is not available or is unsuccessful, the only option is to manage the incontinence events themselves. This typically involves the sufferer wearing an absorbent pad or diaper. Most adult sufferers of incontinence are elderly or suffer from some form of disability. Therefore, a significant portion of patients in care institutions such as hospitals, nursing homes, aged care facilities, geriatric institutions and the like suffer from various incontinence conditions.

To comply with regulations and protocols to ensure that these patients are adequately cared for, it is necessary for staff to conduct manual checking of patients suffering from incontinence. This must be done on a regular basis. Manual checks are typically carried out irrespective of whether the patient is known to have suffered an incontinence event, as often the patient is unwilling or unable to alert staff of the fact that an incontinence event has occurred. The need to conduct regular checks of patients for incontinence places a significant drain on the resources available in patient care institutions and also causes inconvenience and disruption to the patient, particularly while resting and during sleep. Manual checks by their nature will vary as to how well the checking is carried out and recorded and will therefore directly affect the efficacy of the care plan that is put in place to manage the patient's incontinence condition; for this reason checking processes that make use of sensor readings that are more reliable can be more effective.

Incontinence indicators and detection systems exist. Often these are complex sensors which are expensive and require manual insertion to a diaper or other absorbent article worn by the subject. Such sensors often involve complex arrangements of passive and/or active electronic components and as such, can require significant labour and material costs of production, in addition to the effort required to manually insert the sensor device into the diaper before it can be worn by the incontinent subject.

Automated incorporation of sensor devices into absorbent articles/diapers is complicated by the fact that these products are manufactured at high speed on an assembly line which typically turns out between 300 and 500 units per minute. Diaper assembly lines use an in-line process in which individual pad layers are fed from rollers, including compression and tension rollers which apply and adhere the various diaper layers together. Generally there is little lateral or longitudinal precision involved with this process and so it is difficult to reliably insert and position sensing components during the regular diaper manufacturing process. For these reasons, manually inserted sensors continue to be the preferred method of manufacture for sensors monitoring the wetness status of individuals suffering from incontinence conditions.

It would be desirable to provide a sensor design and/or manufacturing methodology which overcomes, ameliorates or at least improves upon the existing devices and their methods of fabrication and/or insertion into diapers and other absorbent articles.

The discussion of the background to the invention included herein including reference to documents, acts, materials, devices, articles and the like is intended to explain the context of the present invention. This is not to be taken as an admission or a suggestion that any of the material referred to was published, known or part of the common general knowledge in the patent area as at the priority date of any of the claims.

SUMMARY OF THE INVENTION

Viewed from one aspect, the present invention provides a sensor device for sensing wetness in an absorbent article worn by a subject, the sensor device including: one or more sensing elements; and a coupling for communicating sensor signals between the one or more sensing elements and a receiver. A change in environmental parameter causes a change in electrical behaviour of at least one of the sensing elements which behaviour can be analysed to determine occurrence of a wetness event in the absorbent article. The changes in electrical behaviour are communicated in the sensor signals to the receiver.

The sensor device may be fabricated into a flexible insert attachable to an absorbent article or other garment worn by a subject. Alternatively, the sensor device may be incorporated into the absorbent article during manufacture of the absorbent article itself. The environmental parameter being sensed is typically wetness but may alternatively/additionally include e.g. temperature or other parameters such as pH, presence of biological analytes or pathogens, odour, changes in pressure or the like.

In one embodiment, a sensing element of the device includes a capacitor formed by first and second conductive members with a dielectric region there between and the change in electrical behaviour is observable as a change in capacitance arising from a change in the permittivity of the dielectric region. Typically the dielectric region contains absorbent fill which becomes wet with an evacuation from the subject thus causing a change in permittivity which, in turn, causes a change in capacitance measurable between the conductive members. In one embodiment the first conductive member is a substrate or base layer of the absorbent article, and the second conductive member is a conductive intermediate layer manufactured into the absorbent article. Ideally such conductive intermediate layers are permeable to liquid so as to minimise impact on the absorbent performance of the absorbent article. Permeability may be achieved e.g. by holes or channels in the conductive layer through which liquid may pass, and be drawn into the absorbent layers of the pad/diaper.

The sensor device may include one or more spacers for substantially maintaining a known distance of separation between the first and second conductive members. This is desirable to maintain symmetry and to avoid the distance between the conductive members changing unpredictably and unevenly (thus affecting the characteristic or baseline capacitance value of the sensing element) e.g. during movement of a subject wearing the absorbent article. A spacer may be a grommet, baffle, film, layer or the like.

Alternatively, artefact arising from changes in capacitance caused by movement of the subject may be compensated for or removed by including a third conductive member/capacitive plate within the sensor element, adjacent the first and second conductive members. In this arrangement the dielectric medium between the second and third conductive members is well defined and sealed to prevent the ingress of moisture from wetness events, thereby forming a reference capacitor. The change in capacitance of the reference capacitor is factored against a baseline value that represents the capacitance prior to external environmental effects with the resultant factor applied to the change in capacitance measurable between the first and second conductive members to compensate for the external environmental factor/s.

In another embodiment, artefact arising from changes in capacitance caused by external environmental factors such as movement of the subject may be compensated for or removed by including a third conductive member/capacitive plate within the sensor element, between the first and second conductive members. In this arrangement, the electrical behaviour is measured as a relative change in capacitance measurable between the first and second conductive members and one of (i) the third and second conductive members; or (ii) the first and third conductive members.

In a preferred embodiment, the electrical behaviour of the sensing element which is monitored to detect wetness is a resonance characteristic. Thus, a change in an environmental parameter (such as moisture or temperature from a wetness event) causes a change in resonance behaviour such as resonance frequency or Q-factor of a sensing element. Other changes in electrical behaviour that may be detected include the load seen by the receiver, current drawn from a signal source, excitation frequency required to attain resonance, impedance in the secondary circuit, magnetic field strength, electric field strength and patterns or signatures of the above observable over time and/or frequency. The change in electrical behaviour may be analysed by a processing means associated or in communication with the sensor element. Such processing means may, for example, be incorporated into a receiver.

In a preferred embodiment, the sensor device is configured to detect wetness in the absorbent article with spatial resolution such that signals from the device facilitate identification of an area within the pad/diaper in which the wetness has been detected. In such an embodiment the sensor device may include a plurality of spaced apart sensing elements each having a different characteristic resonance behaviour. The spacing apart may place sensing elements in a single layer or plane of the absorbent article but spaced e.g. from front to back of the article. Alternatively/additionally, the spacing apart may locate sensing elements in different layers of the absorbent article to provide depth resolution.

In another preferred embodiment of the invention, the sensing elements include capacitors, and at least one, if not all, of the capacitive sensing elements have a plurality of interdigitated capacitive fingers. Each of the capacitors is paired with an inductive component to form a resonance circuit. Ideally, the interdigitated fingers and other components in the sensing element are planar so as to provide a sensing element which is, overall, substantially planar. Substantially planar sensing elements may be more easily fabricated into an absorbent article during the production process. It is also less likely to affect the subject's comfort while an absorbent article containing the sensing elements is being worn. In one embodiment, each "plate" of a capacitive sensing element is encapsulated in a liquid impermeable layer, or is electrically isolated from moisture in the absorbent article, although wetness may still flow between the plates.

Sensor signals from the one or more sensing elements are communicated to a receiver via a coupling. The coupling between the sensing elements of the sensor device and the receiver may be a contact coupling or a contactless coupling. A contactless coupling is ideally of the inductive kind, which facilitates inductive energy transfer between the sensing elements and the receiver, although other types of contactless coupling are also possible. Thus, there may an inductive component in the form of a coil formed around, adjacent to or distal from and substantially planar with the sensing element. Placement of the inductive component facilitating communication with the receiver is ideally such that a corresponding receiver coil can be placed over the inductive component for transmission of energy between them, thereby facilitating transmission of the sensor signals to the receiver.

An alternative contactless receiver coupling may be achieved by providing an inductive component that is formed on or into an antenna attachment which may be placed over a surface of the absorbent article such that the antenna circumscribes an area in which the sensing elements and their transmission coils are located. The antenna attachment may include a substrate onto or into which the inductive component/transmission coil has been formed, which substrate may be held in place with an adhesive in a manner similar to application of a panty liner, napkin or the like.

Ideally, the antenna attachment is on the external side of the absorbent article during wearing to avoid adversely affecting the absorbent performance of the article. In one arrangement, the antenna attachment is incorporated into a garment, such as an overpant worn over the absorbent article by the subject. This substantially maintains the positioning of the antenna relative to the sensing elements in/on the absorbent article. Ideally, the antenna attachment includes a contact coupling for forming an electrical connection with a receiver with which the sensor device may be used.

In certain embodiments, the sensor device may include one or more flow control features. Ideally, these features encourage discretised spread of moisture over a surface of a conducting member in a sensing element. The one or more flow control features may include but are not limited to surface features in a cover layer over the conducting member which define boundaries across which liquid less readily flows; and/or chemical or charged features in a cover layer applied to, or over, the conducting member. Alternatively the surface features or the chemical or charged features may be formed in or on the conducting member itself. These features define boundaries across which liquid less readily flows. In a sense, the features form what may be referred to as capillary barriers. Ideally, the flow control features are arranged to form a grid over the conducting member.

In certain embodiments, the sensor device may include a compensating reference element that is isolated against a parameter that is being measured, yet which is affected by external environmental effects in a manner similar to the sensing elements themselves. Thus, the reference element provides an indicator of the impact of the external environmental effects on the performance of the sensing element. This indicator may be used in analysis or processing, to compensate sensor device signals for the impact of external environmental effects on the focal parameter being measured.

Viewed from another aspect, the present invention provides a method for fabricating an absorbent article incorporating a sensor device as described herein. The method includes fabricating a continuous length of material incorporating a plurality of spaced apart sensing elements, spooling the fabricated material onto a roll, and then incorporating the spooled material into the inline feedstock of a production facility producing absorbent articles. It is to be noted, however that in some production facilities the spooling step may be omitted. Preferably, the sensing elements are spaced apart in a pattern or layout which reduces stacking of sensing elements or parts thereof when the fabricated material is spooled onto a roll. Spacing apart of sensing elements may be in a single layer. Alternatively/additionally they may be spaced apart by placement in different layer depths, such as an inside (patient side) layer and the outside layer.

Viewed from another aspect, the present invention provides a method for fabricating an absorbent article incorporating a sensor device as described herein. The method includes fabricating a continuous length of material incorporating a plurality of spaced apart sensing elements, and folding the fabricated material in a zigzag manner into a heap, and then incorporating the heap of folded material into the inline feedstock of a production facility producing absorbent articles. Preferably, the sensing elements are spaced apart in a pattern or layout which reduces stacking of sensing elements or parts thereof when the fabricated material is folded into the heap, for space efficiency.

Alternatively/additionally, the fabrication method may include operating a placement device to generate a negative pressure or vacuum for releasably collecting a sensing element, placing the collected sensing element in a desired location on a layer of feedstock for the absorbent article and releasing the sensing element onto the feedstock to form fabricated material used in making the absorbent article. Preferably, an adhesive is applied to the sensing element before the releasing step.

In one embodiment, a registration mark is provided on the fabricated material and is used for placement of a cutting blade prior to using the blade to cut the fabricated material to size. The registration mark may comprise one or more of a notch, hole, slit, protrusion, metallic node, magnetic node, fluorescent marker and a visible or non-visible marker.

Thus, the method may further include rotating a drum having one or more cutting blades to cut the fabricated material into lengths for making individual absorbent articles. Rotation of the drum during cutting may be controlled with respect to a registration mark on the fabricated material so that the cutting blade is correctly positioned before cutting occurs. Correct positioning avoids severing sensing elements within the absorbent article.

In one embodiment, the method includes cutting the fabricated material to portions of a length suitable for incorporation into the absorbent article, placing the cut portion of the fabricated material onto a layer of the absorbent article in fabrication and assembling remaining layers of the absorbent article. The method may involve gluing the layers together using an adhesive, or sealing them together around and/or inside the periphery of the article.

In another embodiment, one or more cut lengths of the fabricated material may be transferred using a negative pressure/vacuum source in a "pick and place" approach to assembly or fabrication of an absorbent article.

In one embodiment, the fabricated material includes one or more identifiers such as a designated cutting zone, a connection zone for a contactless coupling, an identifier of the location of a sensing element within the absorbent article, a batch number of the sensing elements and a performance rating of a sensing element or absorbent article into which a plurality of the sensing elements has been fabricated. A connection zone for contactless coupling may employ tactile or physical guides for placement of a receiver device containing inductive coils over corresponding (but not visible) coils in the absorbent article when it is in use. The tactile or physical guides may employ e.g. holes or notches formed in the fabricated material into which protrusions in the receiver clamp are inserted during coupling.

Viewed from yet another aspect, the present invention provides an antenna attachment for transmission of energy between one or more sensing elements configured to sense wetness events in an absorbent article worn by a subject, and a coupling to a signal source device. Ideally, the signal source device also behaves as a receiver for the return signals from the sensing elements. The antenna attachment includes a substrate, a coupling for connecting the antenna attachment with a signal source device for current flow there between, and an inductive coil fabricated on or into the substrate. The inductive coil has sufficient turns for inductive energy transfer between the one or more sensing elements and the signal source device.

The substrate may be a flexible layer formed from a material selected from the group including but not limited to a polymer, a non-woven material, a woven material, paper and hemp. In one embodiment, the substrate comprises a garment such as an overpant worn by a subject over an absorbent article. In another embodiment, the substrate is a pad or napkin or the like which is removably attachable e.g. to an external surface of an absorbent article worn by the subject. In the latter embodiment, the substrate may be attachable by means of adhesive backing on one of the substrate of the antenna attachment and the absorbent article.

The inductive coil may be fabricated into the substrate using a conductive thread or ribbon such as e.g. copper, silver or gold which is woven or stitched into the material of the substrate. In embodiments where the antenna attachment is a reusable garment, it is desirable for the inductive coil to be sufficiently robust that the garment can be laundered and/or flexed/folded without degradation or breaking of the inductive coil. Alternatively, the inductive coil may be fabricated onto the substrate by using printed inks, ribbons, threads and the like.

BRIEF DESCRIPTION OF THE DRAWINGS

The present invention will now be described in greater detail with reference to the accompanying drawings. It is to be understood that the embodiments shown are examples only and are not to be taken as limiting the scope of the invention as defined in the claims appended hereto.

Figure 1A:
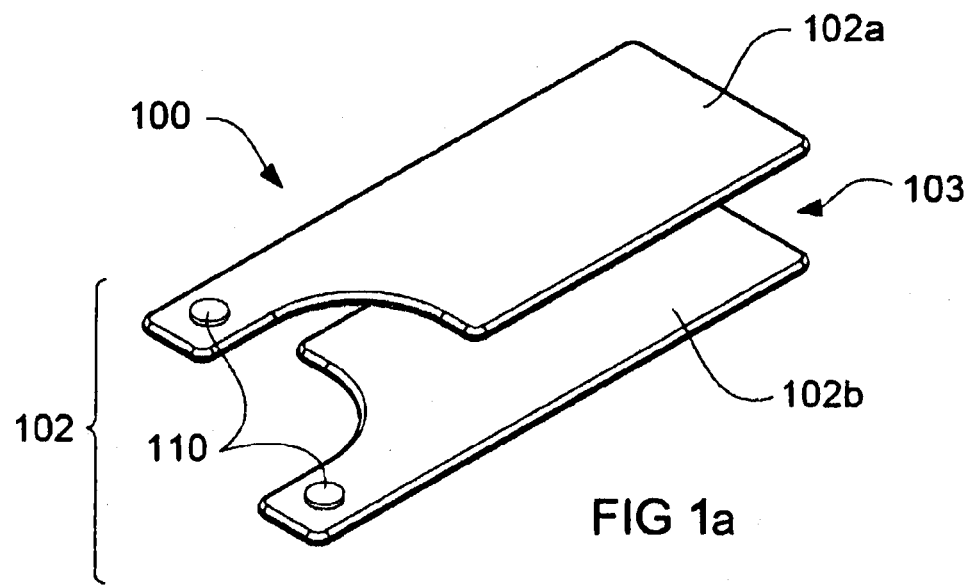
FIG. 1a is a schematic drawing of a sensing element comprising a capacitor for contact coupling with a receiver. FIG.

1b is a schematic drawing of a sensing element like the one in FIG. 1a, but configured for contactless coupling with a receiver.

Figure 2A:
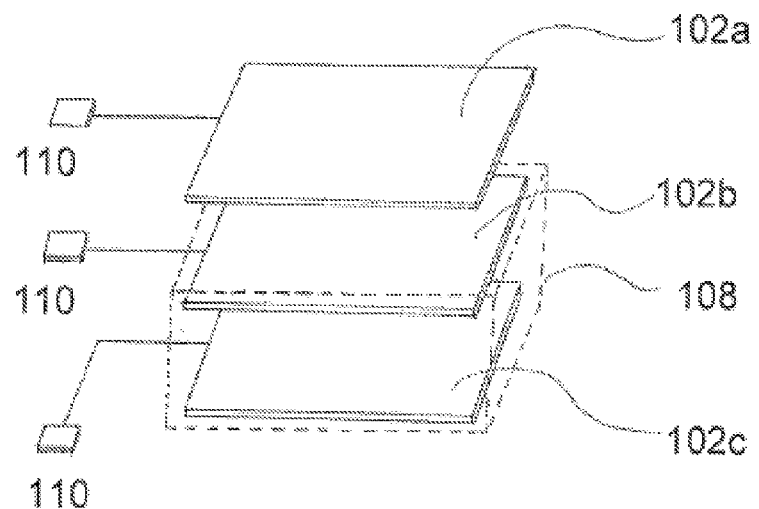
Figure 2B:
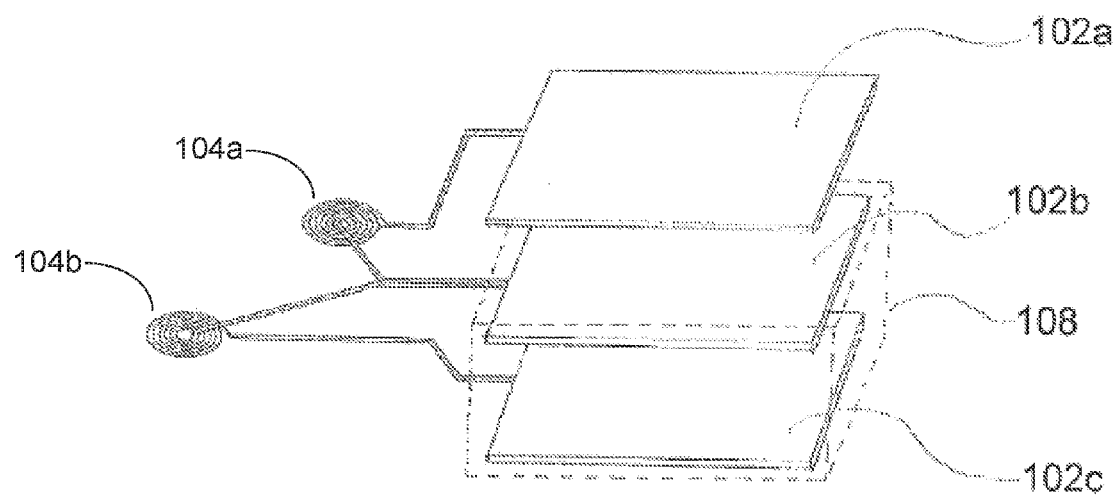

FIG. 2a is a schematic drawing of a sensing element comprising a capacitor with three conductive members, wherein the second and third conductive members form a sealed reference capacitor, and configured for contact coupling with a receiver, according to another embodiment of the invention. FIG. 2b is a schematic drawing of a sensing element like the one in FIG. 2a but configured for contactless coupling with a receiver.

Figure 3A:
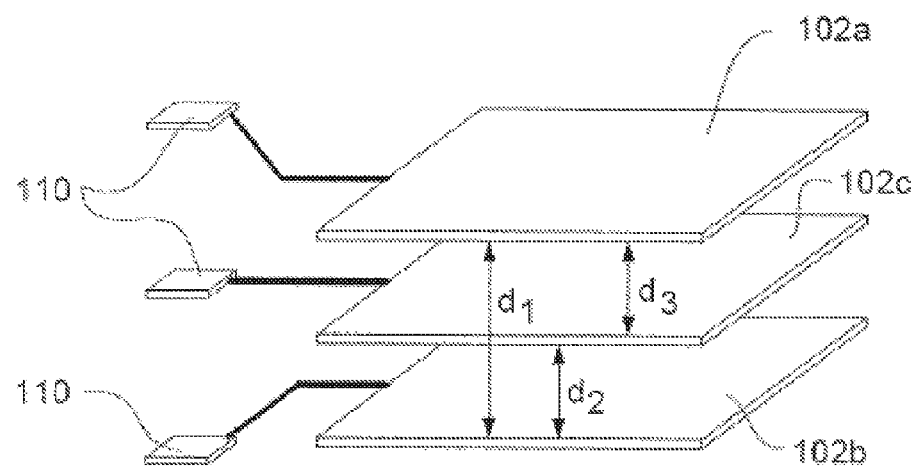
Figure 3B:
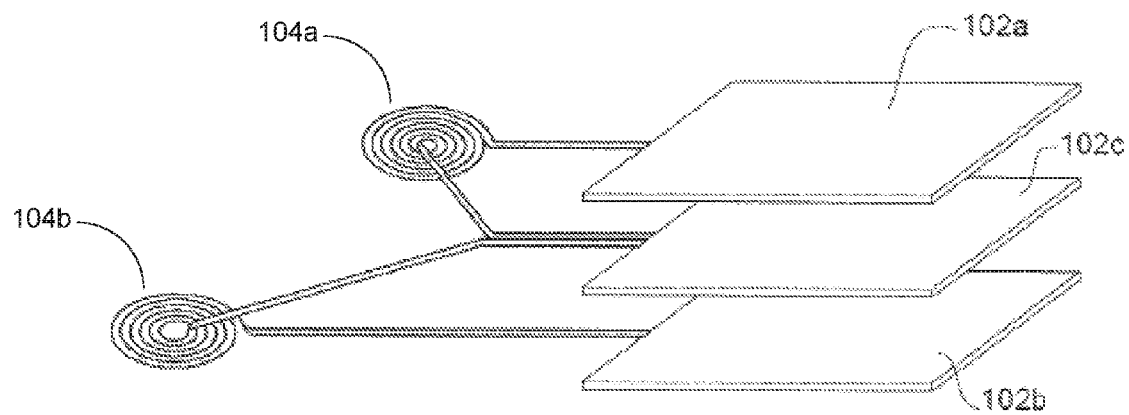

FIG. 3a is a schematic drawing of a sensing element comprising a capacitor having three conductive members, and configured for contact coupling with a receiver, according to another embodiment of the invention. FIG. 3b is a schematic drawing of a sensing element comprising a capacitor having three conductive members like the one in FIG. 3a, and configured for contactless coupling with a receiver, according to yet another embodiment of the invention.

Figure 4:
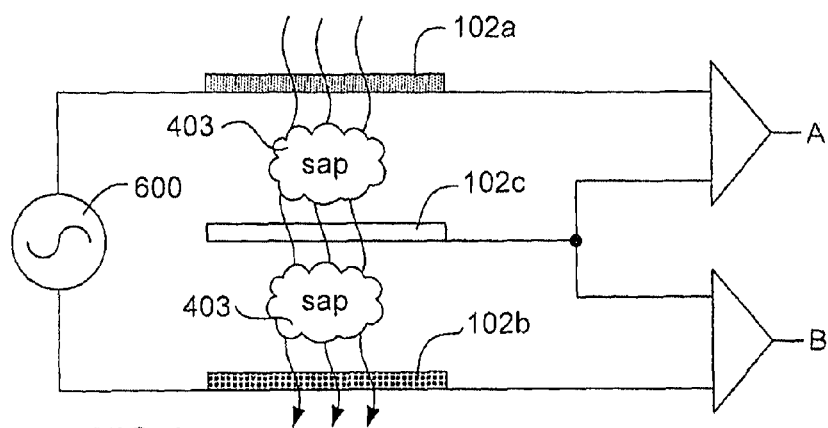

FIG. 4 is a simplified circuit diagram showing components of a differential capacitance sensor element, corresponding to FIGS. 3a and 3b.

Figure 5:
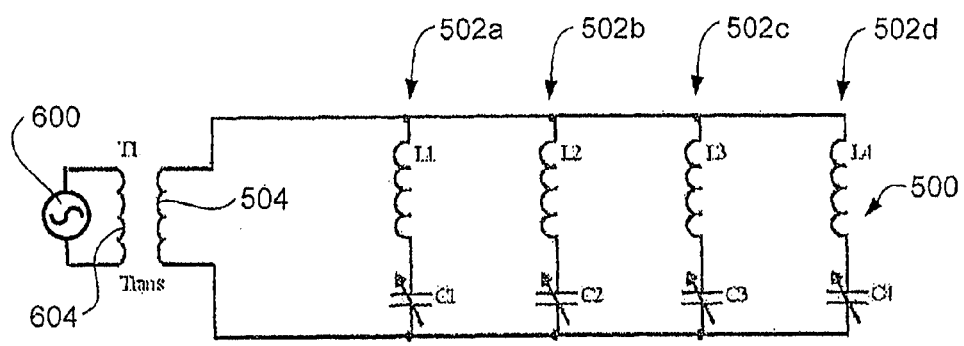

FIG. 5 is a circuit diagram showing four resonance circuits connected in parallel and configured for contactless coupling with a receiver.

Figure 6:
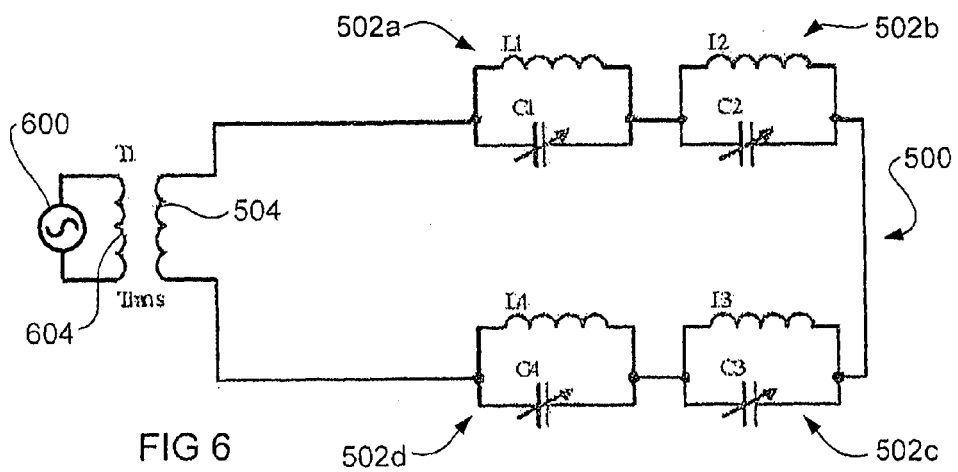

FIG. 6 is a circuit diagram showing four resonance circuits connected in series and configured for contactless coupling with a receiver.

Figure 7A:
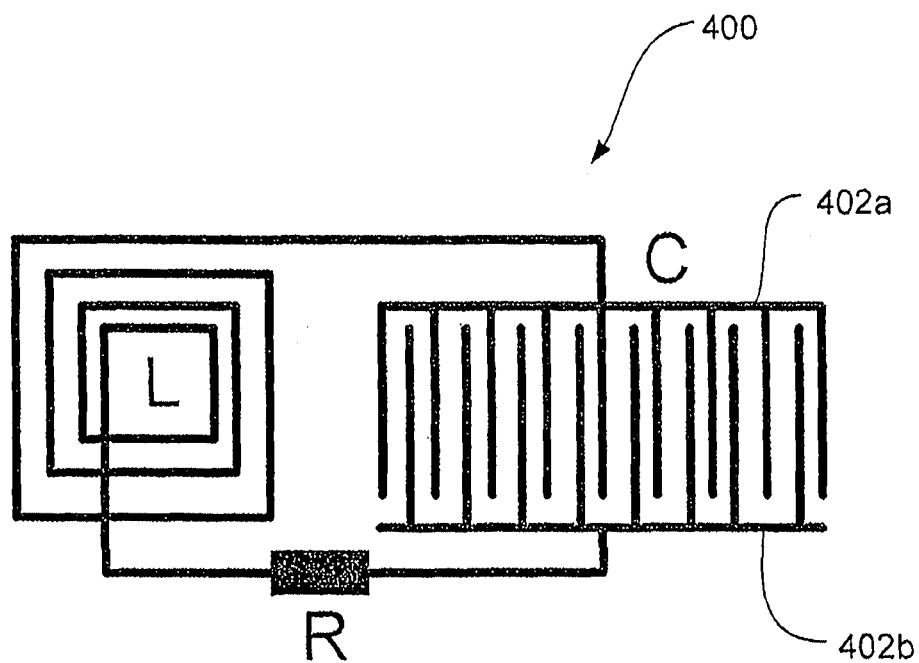
Figure 7B:
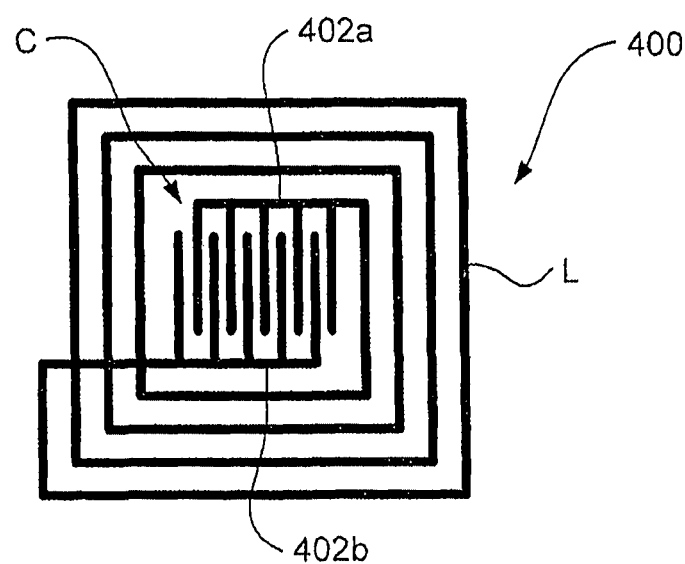

FIGS. 7a and 7b are simplified diagrams of sensing elements comprising inductive, capacitive and resistive components, according to embodiments of the invention.

Figure 8A:
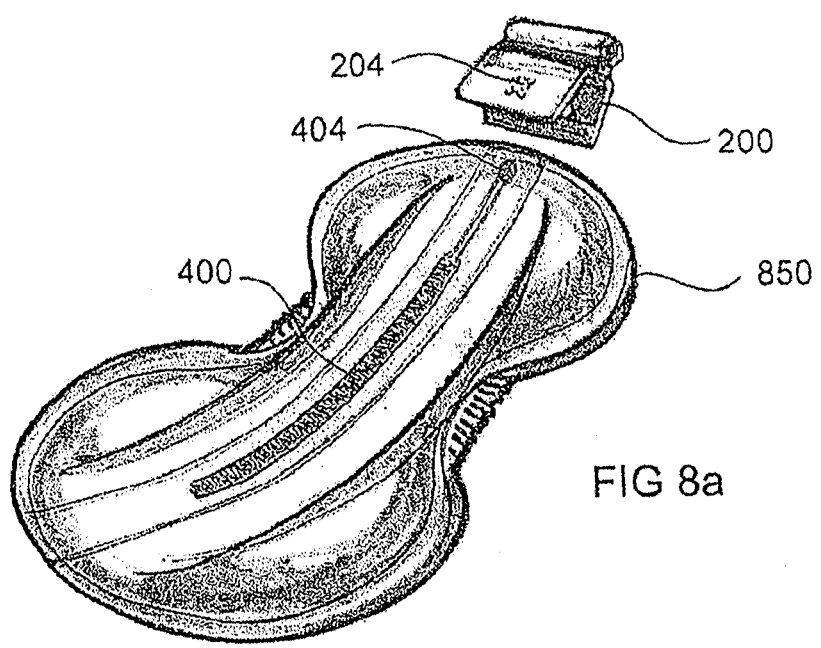
Figure 8B:
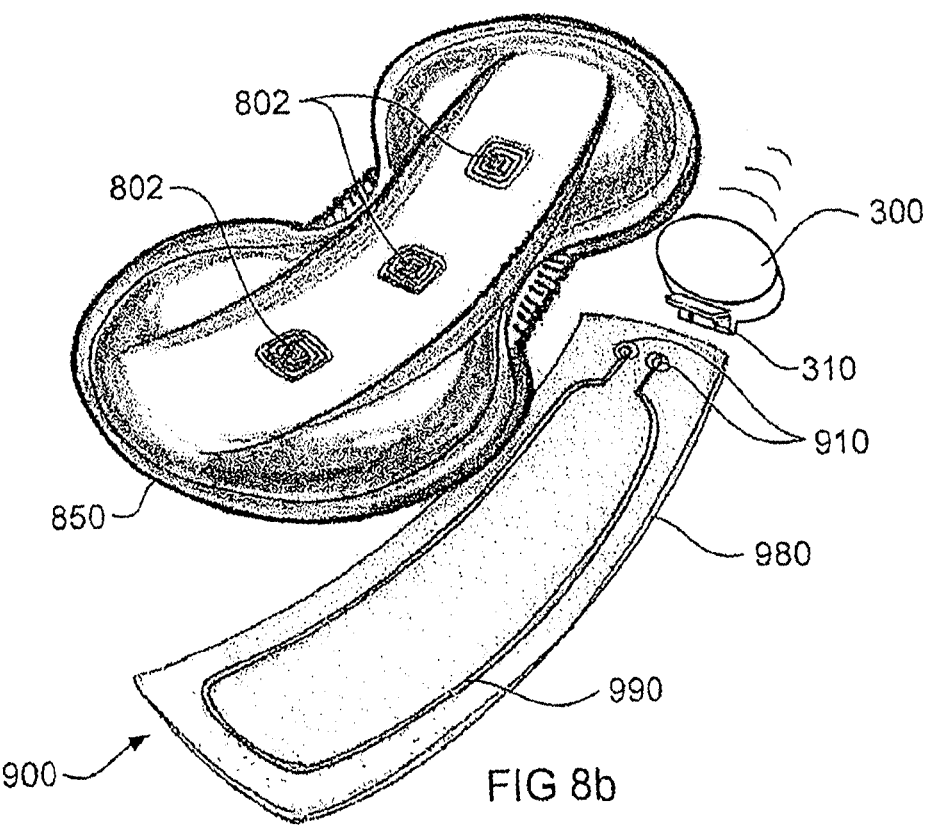

FIG. 8a is a schematic illustration of an absorbent article having a sensing element in the form of an elongate interdigitated capacitor and contactless coupling with a receiver. FIG. 8b is a schematic illustration of an absorbent article having three sensing elements and used with an antenna layer, according to an embodiment of the invention.

Figure 9A:
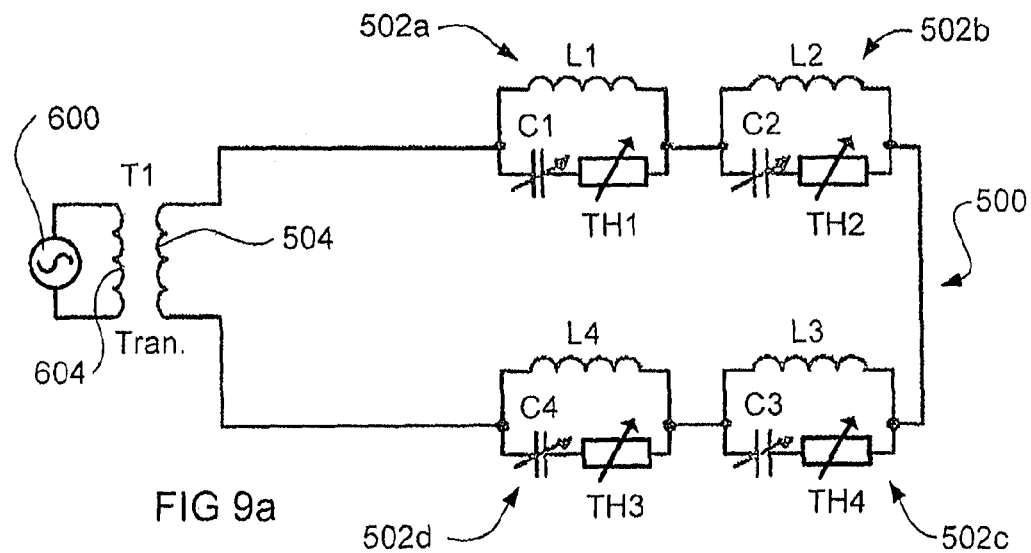
Figure 9B:
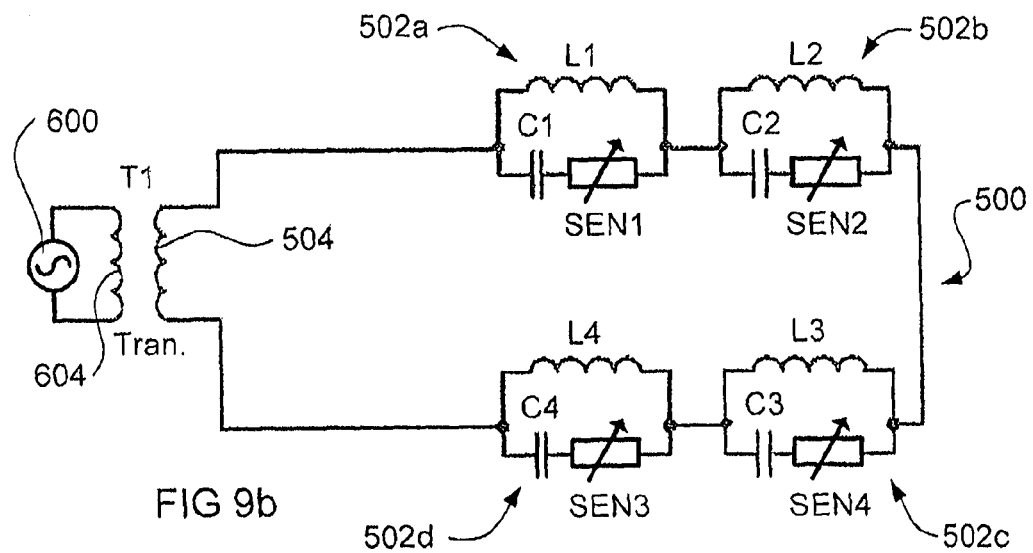

FIG. 9a is a circuit diagram showing four resonance circuits connected in series and incorporating thermistor elements for sensing temperature. FIG. 9b is a circuit diagram showing four resonance circuits connected in series and incorporating conductive elements used to detect conductance between exposed conductive elements, to sense wetness.

Figure 10A:
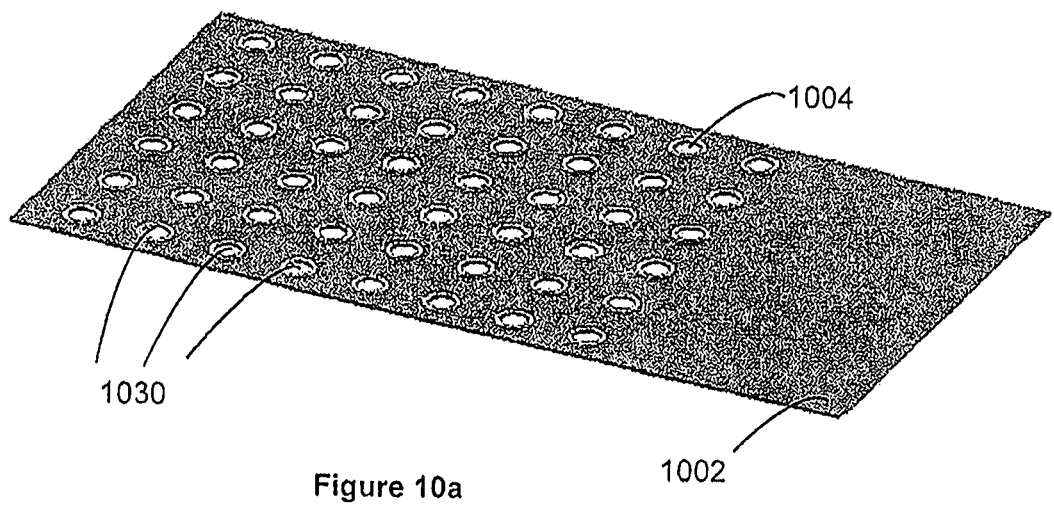
Figure 10B:
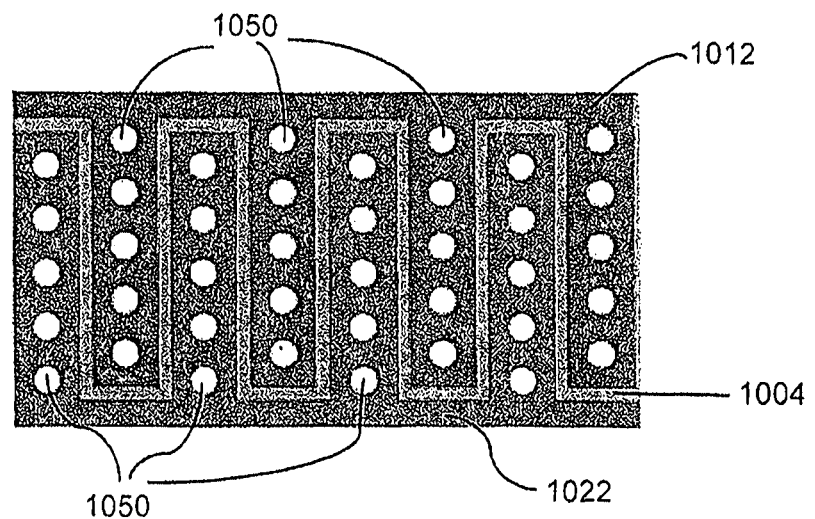
Figure 10C:
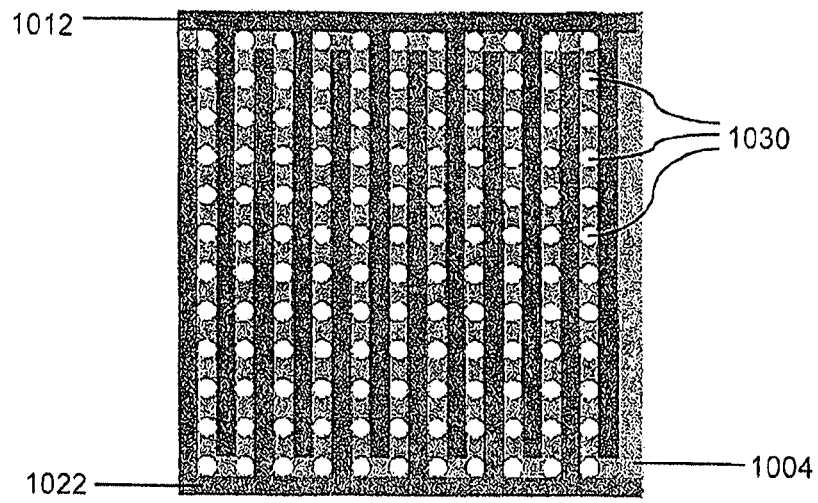
Figure 10D:
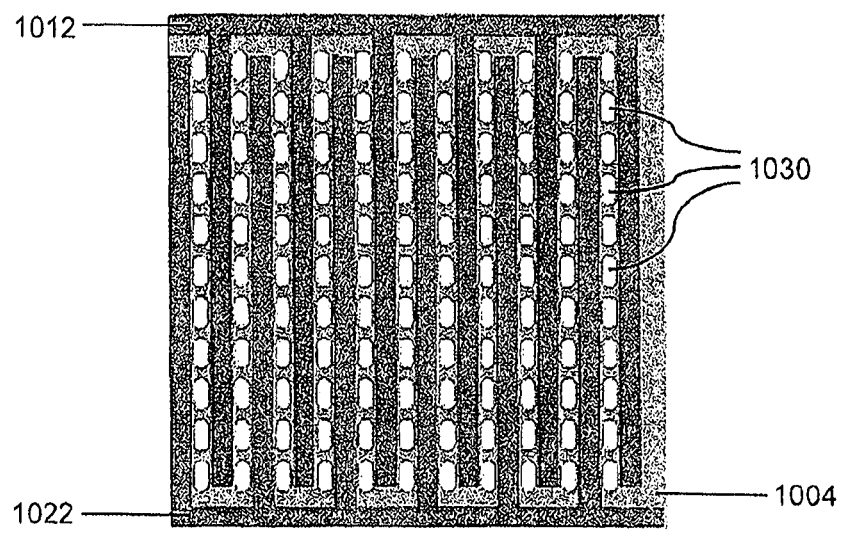

FIG. 10a is a schematic illustration of a conductive member having flow channels according to an embodiment of the present invention. FIG. 10b is a schematic illustration of an interdigitated capacitor having flow channels formed in the capacitor fingers, according to another embodiment of the present invention. FIGS. 10c and 10d show further embodiments of interdigitated capacitors with a substrate layer separating the two conductive members and the substrate layer including flow channels in the form of holes (FIG. 10c) and slots (FIG. 10d) respectively.

Figure 11:
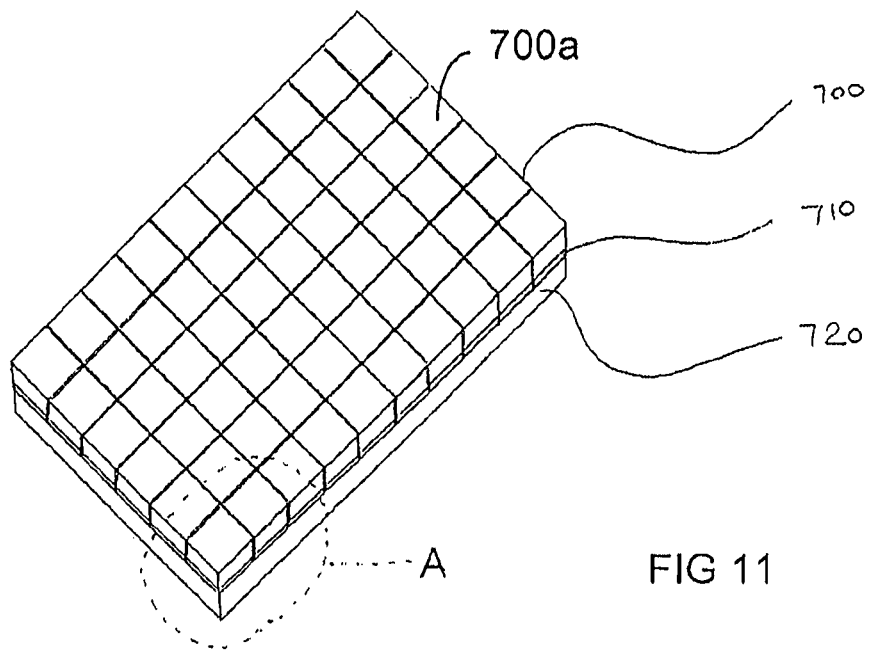
Figure 11A:
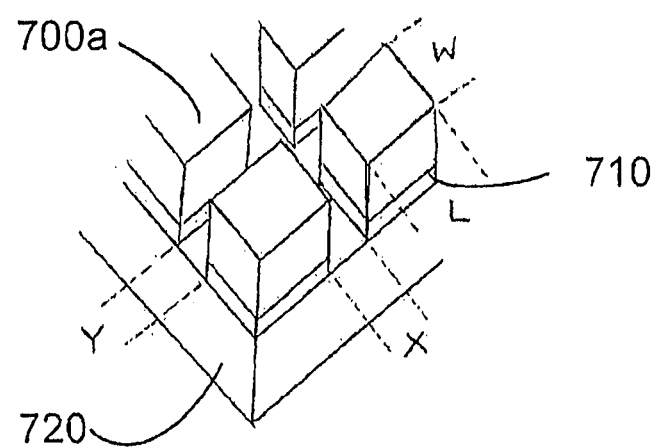

FIG. 11 is a schematic illustration showing a portion of a conductive element with flow control features, according to another embodiment of the invention. FIG. 11a is an expanded view of section A of FIG. 11.

Figure 12:
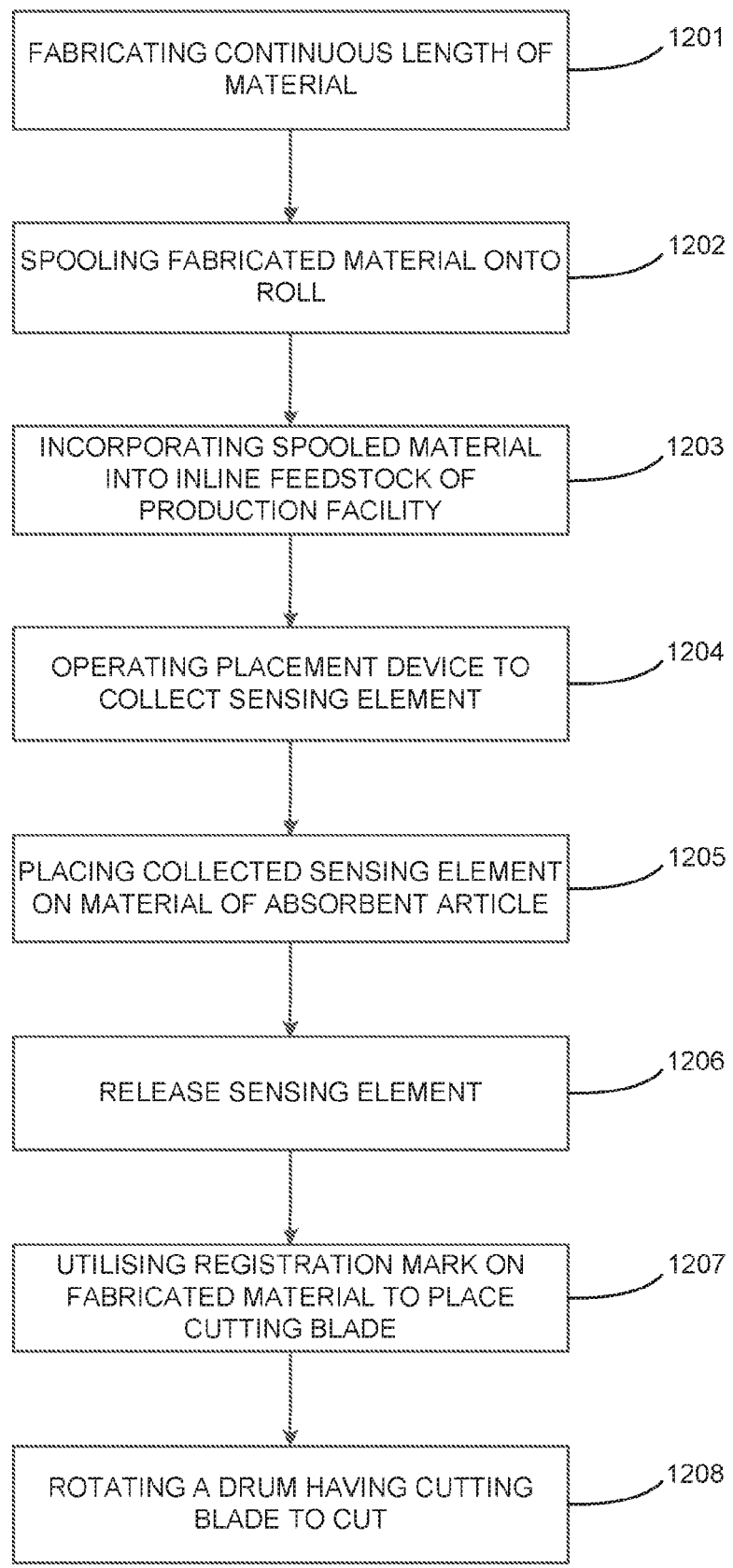

FIG. 12 is a schematic illustration of steps in a method for manufacturing an absorbent article according to embodiments of the present invention.

DETAILED DESCRIPTION

Throughout this description and claims, the term "absorbent article" is used. It is to be taken as including pads, diapers, liners, nappies, dressings, incontinence appliances and other absorbent devices that absorb moisture such as urine, faeces, blood, plasma and the like. The absorbent articles may be worn by adult subjects or babies, children or adolescents as the need may arise. Alternatively/additionally they may be worn by animal subjects.

Referring firstly to FIG. 1a, there is shown a first embodiment of a sensor device 100 for sensing wetness in absorbent article worn by a subject. In the example provided in FIG. 1a, the sensing element is a capacitor 102 formed by a first conductive member 102a and a second conductive member 102b with an interposing dielectric region 103 there between. Although only one sensing element is shown in FIG. 1, it is to be understood that the sensor device 100 may include a plurality of sensing elements 102. Coupling points 110 are provided for coupling the sensing element to a receiver for use with the sensor device. The receiver (not shown) receives signals from the sensing element. The signals are used to determine the presence of wetness in an absorbent article in which the sensing element has been incorporated by detecting in the signal a change in the electrical behavior exhibited by the sensing element or an electric circuit incorporating the sensing element. In this embodiment, the changing electrical behavior can be detected as a change in capacitance.

According to Equation 1 below, the relationship between wetness and capacitance is linear as the wetting substance (mainly water) replaces air in the absorbent fill layer causing a permittivity change proportional to the volume of wetting substance present. In practice, the change in capacitance may depend also on the geometry (i.e. shape) of the wetted region and the capacitance may not exactly be proportional to volume.

Typically, the dielectric region 103 between first and second conductive members 102a, 102b includes part of the absorbent fill or sap of the absorbent article. When a wetness event occurs within the article, the fill layer becomes saturated, either entirely or in part. This changes the permittivity of the dielectric region which alters the capacitance measurable between those members. The equation governing capacitance between two conductive members is:

$$c = \in A/d \qquad \text{(Equation 1)}$$

Where:
C is the capacitance of the element:
A is the overlapping area of the conducting members/plates
$\in$ is the permittivity of the dielectric between the plates 102a, 102b; and
d is the distance between the plates.

The introduction of moisture from a urinary or faecal wetness event when released into the absorbent article, changes the electrical permittivity of the absorbent filler material in the dielectric layer and hence the capacitance of the sensing element. This can be measured directly by attaching a meter across coupling points 110.

Figure 1B:
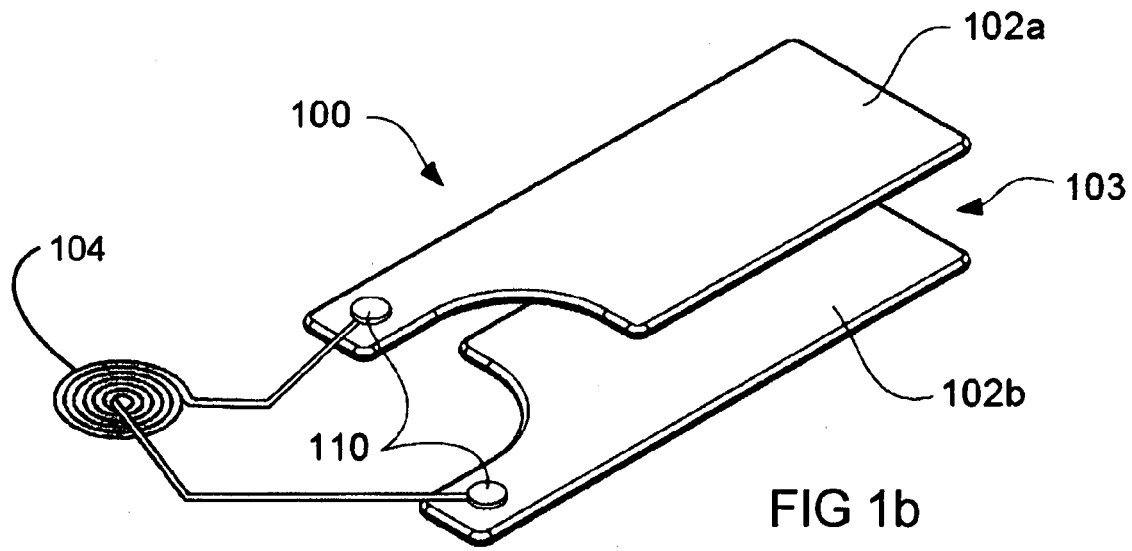

Ideally, the meter is incorporated into a receiver (not shown) which is used with the sensor device. The receiver may be a device including e.g. a meter which measures the capacitance in Nano farads or Pico farads directly from receiver points when brought in electrical contact with coupling points 110 on the sensing elements 102a, 102b. Alternatively/additionally, the receiver may apply a DC charge to one of the conductive members 102a, 102b via coupling points 110 and measure the time for the capacitor to discharge in order to ascertain the capacitance of the sensing element. However, there are safety issues associated with use of DC power supplies in devices that contact human skin. To avoid these, it is desirable that an AC or pulsed current source may be used instead, or that there is no direct electrical connection between a current source (which may be incorporated into the receiver) and the sensor elements in the absorbent article. FIG. 1b shows an embodiment of the invention in which the capacitive sensing element of FIG. 1a is adapted for contactless coupling with a receiver (not shown) via coil 104.

In one embodiment, the receiver includes processing means configured to analyse signals from the sensor device to identify the occurrence of a wetness event and preferably to estimate the volume of an individual wetness event and optionally, the cumulative volume of a plurality of wetness events that have occurred in the absorbent article. Other functionality such as data acquisition, storage and signal processing may also be built into the receiver. Alternatively, part or all of that functionality may be done at a remote device, such as a base station which contains processing means.

Where the receiver is a device worn by the subject, signals from the receiver may be downloaded into a base station by removing the receiver from the subject and connecting it e.g. via a USB cable, Bluetooth, docking station or the like to the base station processor. The base station may be a private computer for home use, or it may form part of a central monitoring station of the kind used in institutional care, where signals from a number of different receivers, represent wetness data for a number of different individuals being monitored simultaneously. The cloud computing environment may also be employed.

In one embodiment, the body-worn receiver is coupled with the base station via a wireless network such as a Wi-Fi, zig-bee or similar wireless LAN, or a wireless WAN such as the 3G and 4G networks or other wireless networks which are available from time to time. Ideally, data obtained from a receiver is processed in real time, although it is also contemplated that data may be obtained from a receiver in batches and subsequently processed offline. Such data processing may be particularly useful in clinical studies and analysis of population data.

In certain scenarios the sensor element in FIG. 1a may not behave as an ideal capacitor i.e. with a fixed distance separating the conductive members. For instance, movement of the subject wearing an absorbent article into which the sensor device has been incorporated or onto which it has been applied may cause the distance between the conductive members to vary and lose symmetry. Varying the distance between the conductive elements, in turn, changes the characteristic capacitance value of the sensing element as governed by Equation 1 even when the element is dry. FIGS. 2a, 2b, 3a, 3b and 4 provide alternative approaches to providing a capacitive sensing element which aim to compensate for changes in characteristic capacitance arising from changes in the distance 'd' between the conductive members.

As an alternative (or in addition) to the differential capacitive embodiment illustrated in FIGS. 2a, 2b, 3a, 3b and 4, spacers may be incorporated between the first and second conductive members 102a, 102b of FIGS. 1a and 1b in order to maintain a substantially constant dielectric distance d, even during movement of the subject.

FIG. 2a shows an alternative embodiment of the invention. In FIG. 2a the sensor element is similar to that shown in FIG. 1a and further includes a third conductive member 102c positioned adjacent, to form a second capacitive element, between second and third conductive elements 102b and 102c. This second capacitive element formed by elements 102b and 102c is sealed from the ingress of wetness by water impermeable sheath 108, and has a well-defined dielectric between conductive members 102b and 102c to form a reference capacitor that will vary with the movement of the subject, but not with wetness. Changes in capacitance of the reference capacitor attributable to non-wetness related environmental effects are factored against a value that represents the baseline capacitance value measured prior to external environmental effects. The resultant factor is then applied to the change in capacitance measurable between the first and second conductive members 102a and 102b, therefore compensating the measured capacitance between 102a and 102b for non-wetness related external environmental effects such as subject movement.

In FIG. 2a, coupling points 110 are provided for coupling the sensor element to a receiver. FIG. 2b shows the same sensing element of FIG. 2a, but with coils 104 in place of contact points 110, enabling contactless coupling with a receiver.

FIG. 3a shows a further embodiment of the invention. In FIG. 3a the sensor element is similar to that shown in FIG. 1 and further includes a third conductive member 102c positioned between the first and second conductive members 102a, 102b. In this arrangement, the electrical behaviour which indicates a change in wetness or the occurrence of a wetness event is measured as a relative change in capacitance between, on the one hand: the first and second conductive elements 102a, 102b across distance d1; and on the other hand: either the third and second conductive elements 102c, 102b across distance d2, or the first and third conductive elements 102a, 102c across distance d3.

Thus in one arrangement, the capacitance between the first and second conductive members 102a and 102b (i.e. the outer plates) is measured and the capacitance between the second and third plates 102b and 102c (bottom and central plates) is measured. Changes in the distance between conductive members due to movement will typically affect the relative distances between both sets of plates. However, the ratio of the two capacitance values measured across d1 and d2 or d1 and d3 should remain substantially constant where the third conductive member 102c remains equidistant from the first and second conductive members either side of it. Thus, a relative or differential capacitance measurement between these plates may be utilised to indicate the change in electrical behaviour brought about by wetness. In FIG. 3a, coupling points 110 are provided for coupling the sensor element to a receiver. FIG. 3b shows the same sensing element as FIG. 3a, but with coils 104 instead of coupling points 110, enabling contactless coupling with a receiver.

FIG. 4 is a schematic diagram of a differential capacitor sensor circuit representing components of the sensor device including the sensing element shown in FIGS. 3a and 3b. Sap fill material 403 appears on either side of conductive member 102c. Movement of the subject appears as a common mode signal measurable at 600 between all layers of the pad, whereas changes in permittivity and hence capacitance arising from wetness in the sap layer(s) 403 appear as a differential signal measurable between outputs A and B.

In the embodiments shown in FIGS. 1a, 2a and 3a, the conductive members 102a, 102b, 102c forming capacitive sensing element 102 are configured for direct coupling with a receiver using contact coupling points 110. Direct coupling may utilise any suitable form of electrical contact such as clamps, clips, hooks, or the like which enable a releasably connectable receiver to form a physical electrical connection with and thus monitor the sensing element 102 for changes in electrical behaviour which indicate the occurrence of a wetness event in the absorbent article. In one embodiment, this requires the edges of the conductive members to extend beyond an edge of the absorbent article for direct electrical connection to a contact coupling in the receiver. Alternatively, connecting strips, tracks or other elements may connect the edges of the conductive elements 102a, 102b, 102c to a coupling point 110 for connection to a receiver.

In the embodiments illustrated in FIGS. 1a, 2a and 3a, the large surface area of the capacitive plates provided by each of the conductive members 102a, 102b simplifies connection with a receiver by direct, i.e. contact coupling with the sensing element 102 at coupling points 110. However, there is a possibility that incorporating a third conductive member 102c into the absorbent layers of the pad may introduce fabrication complexities that are not easily dealt with.

Sensor devices according to embodiments of the invention, i.e. incorporating the capacitive components provided by conductive members 102a, 102b and 102c may be manufactured using a multi-layer approach, e.g. where a base layer of the absorbent article forms one of the conductive members and a second and optionally third conductive member is fabricated into the absorbent article during the inline pad manufacturing process. This technique requires modification of existing pad manufacturing plants to incorporate the materials into the overall production process. Where two conductive members are used, two insertion stations are required in the production line. Where three conductive members are used (as in FIGS. 2a, 2b, 3a and 3b), a further insertion station is required. Given the capital cost associated with modification of a pad production facility in this way, it may be desirable to limit the number of insertion stations required.

Thus, it may be preferred that one of the conductive members forms a substrate layer of the absorbent article, so as to replace one layer in the manufacturing process. Where a conductive member forms an external layer or substrate of the pad it is desirable that it is substantially non-permeable to exudates arising from incontinence events to avoid wetness passing all the way through the absorbent article. However, where second and third conductive members are fabricated into the article as intermediate layers, it is desirable that these are permeable to liquid so as to minimise interference with usual performance of the absorbent article in trapping moisture from the subject and/or wicking it away from the subject's skin. In some embodiments, the conductive members may be hydrophilic to draw liquid away from the subject and toward the sensing elements. The conductive members could be hydrophilic as a result of inherent hydrophilic properties of the members themselves and/or a substrate or material incorporated into the members. Alternatively/additionally, the conductive members may possess hydrophilic properties by virtue of being covered, coated or laminated with a hydrophilic material or substance. Alternatively/additionally, the conductive members may be provided with slots, holes, pores or channels facilitating flow of moisture across the member and into the absorbent article.

FIGS. 1a, 2a and 3a show arrangements for contact coupling with a receiver using contact points 110. FIGS. 1b, 2b and 3b show an alternative to contact points 110, in the form of coils 104, 104a and 104b for contactless coupling between the sensor device and a receiver provided for use with the sensing device. In this arrangement, first and second plates 102a, 102b are connected to inductive components illustrated as coils 104a, 104b. In FIG. 3b, both inductive components 104a, 104b are connected to the third conductive plate 102c to facilitate measurement of the common mode voltage as described above. The coils 104a permit inductive coupling with a corresponding receiver coil in a receiver device with which the sensor device is used. The same or similar contactless coupling approach used to derive the design in FIG. 3b from FIG. 3a can be also be applied to the designs in FIGS. 1a and 2a to create designs in FIGS. 1b and 2b respectively.

Contactless coupling of this (or similar) kind can be advantageous because it eliminates the need for exact registration between layers of an absorbent article or "pad" which are necessary for effective contact coupling. Precise registration of pad layers can be difficult to control during manufacturing due to use of compression and tension rollers during the pad manufacturing process. The inventors have realised that this need for registration and alignment may be done away with if contactless coupling between the sensor device and the receiver can be achieved.

Thus, in a preferred embodiment the sensor device is configured to operate with a receiver device incorporating an inductive component (i.e. receiver antenna) for receiving signals from one or more inductive components (i.e. transmitter antennas) associated with the sensor device without direct contact coupling with the receiver. A clamp, clip or similar releasable fastener which is provided on or in contact with the receiver may be used to position the receiver antenna (primary inductor coil) over one or more transmitter antennas (secondary inductor coils) connected to the sensing elements. A clamp may contain a magnetic core material (such as ferrite or iron powder) shaped to increase the coupling efficiency between receiver and transmitter antenna and to decrease the losses (HF transformer). Once the receiver is applied to the absorbent article in the region in which the coils 104a, 104b have been fabricated, the signals wirelessly received by the receiver antenna are provided to a processor associated with or incorporated into the receiver for detection of changes in electrical behaviour in the sensor element/s.

Although there may be physical connection between the receiver antenna and the processor, in the embodiment illustrated in FIG. 3b (and in FIGS. 5 to 8), there is no physical coupling between the receiver device and the sensor elements 102a-c, 400, 402a-b or 502a-d. Thus, exact registration of layers containing sensing elements is not necessary during the manufacturing process. It is merely necessary for there to be alignment between the inductive transmission coils comprising primary (transmitter) and secondary (receiver) coils during use of the sensor device, i.e. when transferring energy between the sensor device and the receiver.

In a preferred embodiment of the invention, the sensor device includes a plurality of sensing elements and the electrical behavior being monitored to detect wetness is a resonance characteristic. Thus, in a preferred embodiment each sensing element in the sensor device ideally includes a resonance circuit.

Resonance circuits can be built up from parallel connected resonance elements, comprised of series connected inductive (L) and capacitive (C) components as is shown in FIG. 5. Alternatively, resonance circuits can be built up from series connected resonance elements comprised of parallel inductive (L) and capacitive (C) components as illustrated in FIG. 6. In each case, the capacitor-inductor pair provides a resonance circuit which can be utilized as a sensing element of a sensing device according to an embodiment of the invention. In certain embodiments, the sensing element may also incorporate a resistive (R) or other component which may be employed to tune the characteristic resonance behavior of the circuit and/or to sense additional factors that may be useful in incontinence detection and management, and/or detection of other conditions. These additional factors may include but are not limited to temperature, presence of a gas, pH, bioanalytes, disease/wellness indicators and the like.

The embodiments described herein generally refer to a change in capacitance as giving rise to a change in electrical (resonance) behavior that can be used to sense wetness. However, it is to be understood that other electrical parameters (e.g. resistance) may change with wetness or other environmental changes (e.g. temperature or odor) which may be sensed to indicate that e.g. a wetness event has occurred, and/or to characterize the event.

By way of example, and as shown in FIG. 9a, resistive elements (TH1, TH2, TH3, TH4), may be incorporated into the sensor, e.g. by printing or depositing the resistive elements together with each sensing element onto a substrate, using thermistor type ink or the like. Using this ink, the component's electrical resistance depends on the temperature and can be used to provide additional information about the temperature local to the thermistor element, as well as wetness sensed by resonance elements 502a-d. Resistance changes cause changes in the damping factor in the resonance circuit that may be detected by the receiver to indicate a temperature change. This can be used to distinguish wetness sensed by a capacitive element which arises from an "original" wetness event, from wetness caused by "back-wetting". This is where the already soaked absorbent fill is compressed and wetness is forced back toward the sensor. Thus, monitoring changes in signal damping, in combination with shifts in resonance frequencies, can be used to indicate if there has been a wetness event and if so, whether the event was 'original' or due to 'back wetting'. Positioning these thermistor enhanced resonance circuits at different locations throughout the pad (e.g. front, middle back) also gives locational specificity, since each circuit can be tuned with different resonance characteristics and can be characterized before use, i.e. during calibration.

Alternatively/additionally, the capacitive sensing element may be combined with a variable resistance, where a change of conductance measurable between conductive elements is used directly to detect wetness. Such an arrangement is shown in FIG. 9b. In this example, the conductive elements (SEN1, SEN2, SEN3, SEN4) are not encapsulated in liquid impermeable material. Rather, they can act as conductors between which a circuit may be connected by way of electrolyte fluid (e.g. urine). In this embodiment, the capability of each resonance circuit to detect wetness is limited to indicate merely the physical zone where the wetness is detected within the absorbent article.

Sensor devices employing resonance circuits in the sensing elements are advantageous in that they are readily amenable to contactless coupling with a receiver. Further, in the arrangements illustrated in FIGS. 5 and 6, the expected range of excitation frequencies utilized would typically be in the megahertz range.

Use of resonance circuits to detect wetness may employ AC or pulsatile excitation and measurement techniques and therefore avoids safety issues associated with use of DC excitation in medical and human-use devices. Ideally, in the case of capacitive/resonance method the conductive members may be covered with protective dielectric layer, insulating the circuit elements from the subject. In a preferred embodiment, the one or more sensing elements (each provided in the form of a resonance circuit) are driven from a signal source device 600 contained within a receiver (not shown) with which the sensor device is used. Electromagnetic energy from the signal source is radiated from coil 604 and received by coil 504 where a current is induced to drive the sensing element. Since energy from signal source device 600 is wirelessly coupled with the sensing elements, the sensing device is safer and more desirable for use in a patient setting. Ideally, the signal source device 600 generates sinusoidal waveforms although other waveforms such as square and saw-tooth waveforms and even pulsatile or impulse signals may be employed as the excitation signal in certain scenarios.

The signal source device 600 is typically in the form of an oscillator which drives the sensing elements. For the circuit shown in FIG. 6, when the sensing elements are driven at their resonance frequency, there is maximum energy transfer to the sensing elements with minimal load seen by the source/oscillator 600. For the circuit shown in FIG. 5, when the sensing elements are driven at their resonance frequency, there is minimum energy transfer to the sensing elements with maximal load seen by the source/oscillator 600.

Ideally, the signal source device 600 also acts as a receiver device. Thus, since it is inductively coupled to the one or more resonance circuits, the signal source can be configured to detect changes in the resonance behavior of each of the sensing elements which can in turn be used to detect wetness. Ideally, each resonance circuit is associated with a different sensing element and these may each be tuned (as would be known by a person skilled in the art) to have different resonance characteristics. Resonance characteristics may include e.g. characteristic resonance frequency and/or Q factor.

Ideally, each sensing element provided in a sensor device according to embodiments of the invention is fully characterized. That is, a characteristic resonance behavior is ascertained for each sensing element in the sensor device in a dry state. This may be achieved by e.g. varying one of the components in the sensing element, while holding all other component values fixed, before the element is used for monitoring wetness. Thus, each sensing element has a known and definable characteristic resonance behavior when the absorbent article is dry. By using different excitation frequencies to excite the sensing elements, the properties including the resonance behavior of the elements can be detected. Resonance properties may also be detected by exciting the sensing element with a wideband impulse such as a step function or narrow pulse.

When wet, the characteristic resonance behavior changes and this may be determined by monitoring a change in load (e.g. power or current drawn from the source 600), or a change in resonance frequency for that sensor element. The extent to which the load or resonance frequency changes may be indicative of e.g. the occurrence of a wetness event and the volume of wetness contained within a wetness event. Ideally, the receiver also contains processing means for creating a time-marked log of signals obtained from each of the sensing elements and these may be used with optimized algorithms to provide e.g. real time estimates of wetness volumes and/or an indication when a cumulative wetness volume from a sequence of events is reaching an absorbent capacity of the pad.

The signal source 600 may provide a single frequency excitation signal to drive the sensing element. However, in a preferred embodiment the signal source drives the sensing elements at a number of different frequencies to ascertain if there has been a shift away from the characteristic resonance frequency and if so, what the new resonance frequency is. The different frequencies may be applied at discrete values. In one preferred embodiment, the signal source device 600 drives the sensing element with a swept frequency signal which ideally includes the resonance frequency of each sensing element in the sensor device to ascertain a) if there has been a change in resonance behavior of the sensing element and if so, b) to ascertain the nature of the change (e.g. the new resonance frequency or new Q factor). A change in resonance behavior may be determined by checking e.g. the amplitude or the current of the received signal. Typically, a change in the resonance frequency value will indicate wetness has occurred in the vicinity of a sensing element.

The swept frequency range applied depends on the size and geometry of the sensor device. A range of 1 MHz to 500 MHz may be useful, more preferably a range of 1 MHz to 5 MHz is likely to work best with the sensing elements, and in particular the likely capacitance ranges of the sensing element designs; this frequency range is believed to have several benefits, including:

1) In conjunction with the sensing element design it helps in minimizing parasitic capacitances which are of less interest with respect to sensing wetness and maximizes capacitance changes that occur in the presence of moisture.
2) Keeping the frequencies below approximately 5 MHz minimizes stray inductances
3) The dielectric permittivity and conductance of water varies sharply with frequency below 40 kHz and above 5 MHz Use of swept frequencies by the signal source device 600 is particularly useful with a sensor device containing a plurality of sensing elements which each has a unique resonance behavior that is individually identifiable by the signal source/oscillator. Alternatively a wideband impulse such as a step function or a narrow pulse can be used as the excitation signal. The sensing element response to such excitation contains information about the resonance behavior of each sensing element. Such response may be analyzed using e.g. Fast Fourier Transform (FFT) and/or other techniques.

A radio frequency (RF) chip may also be incorporated into the sensor device. In such arrangement, the RF chip is coupled with each of the sensing elements in the absorbent article, e.g. by conductive tracks printed on a substrate, or using conductive links, threads or the like. The RF chip may be programmable and thus able to control excitation of each of the sensing elements in time and/or frequency, and collect the sensed signals. The sensed signals may have behavioral variations in e.g. frequency and/or shape and/or amplitude when compared with the excitation signal used. Ideally, the RF chip has the capability to store energy and to transmit energy wirelessly. Energy may be transmitted between the RF chip and a receiver unit (both for excitation of the sensor elements and transmission of sensed signals) across a greater distance than the inductive contactless couplings described above. Hence, use of RF chips for wireless coupling may be more reliable and energy efficient. Using a RF chip may also simplify connection to receivers by removing the need for alignment between corresponding inductive coils in the primary and secondary windings during contactless coupling.

Since the RF circuit has the ability to control excitation signals to each of the resonance circuits in the absorbent article individually, they may in turn exhibit clearer resonance behaviors. This makes signal processing easier to manage. Further, using RF chip technology may address coupling losses observed with use of air cored transformers (such as antenna 990) in inductive couplings as a feedback signal from the RF chip is relatively strong, releasing stored energy during short transmission bursts.

Changes in resonance behavior may involve changes in resonance frequency for a particular sensing element as described above. Alternatively/additionally, changes in resonance behavior may be identified as a change in the load resistance provided by a sensing element as can be determined by monitoring changes in the Q factor of that sensing element. However, measuring the Q of the sensing element is more demanding and requires tighter control of the inductive coupling between the sensing elements and the receiver in which the signal source device 600 is housed. Thus monitoring changes in resonance frequency and resonance frequency peak values (e.g. maxima and minima) and comparing these to the characteristic values when dry is typically more useful and robust.

Where a sensor device incorporates one or more a resonance circuits as the sensing element/s, they may be coupled using contact or contactless coupling by exploiting the inductive element of the resonance circuit. For contact coupling, the sensor elements are directly coupled via coupling points that are in physical electrical contact with corresponding contact points within the receiver. Alternatively, for contactless coupling, the direct physical connection between each sensor element and the receiver is replaced with an inductive coupling of the kind described in relation to FIGS. 1b, 2b and 3b. In one embodiment such as illustrated in FIGS. 5 and 6, an air or solid (ferrite) cored transformer is used to couple each of the sensing elements 502a-d with the receiver, where the primary coil 604 is formed from an inductor in the receiver and the secondary coil 504 is provided in the sensing element, performing the same function as inductors 104, 104a, 104b in the sensor device 500. Tailoring of the inductive coupling may be required, as would be known to one skilled in the art, to correct for lossiness arising from the interconnection.

In a relatively straightforward embodiment, the sensor device may comprise a single sensing element. One such sensing element 400 in the form of a resonance circuit is shown in FIG. 7a. The resonance circuit of FIG. 7a has an inductive component, L; a capacitive component, C; and a resistive component, R. The circuit can be tuned to provide a "characteristic resonance". This can be set by fixing two of the components (e.g. by fixing L and C) and varying the third component (e.g. R). It is hypothesized that controlling the capacitor value C gives preferential control over the resonance characteristics of the sensing element. Further, because of the large surface area of the capacitive component this gives rise to greater sensitivity to wetness entering the absorbent article. Accordingly, in a preferred embodiment it is the capacitance value (and optionally the resistance value) in the resonance circuit that is tuned to arrive at a characteristic resonance behavior for a sensing element. FIG. 7b shows an alternative embodiment in which the inductive element L winds around the planar interdigitated capacitive element, C.

In the embodiment illustrated in FIGS. 7a and 7b, the capacitive component C is in the form of interdigitated fingers forming conductive members 402a and 402b. In one embodiment, the interdigitated fingers of component C, are encapsulated within a water impermeable material and are thus isolated from wetness in the absorbent article. This prevents the components of the sensing element from behaving as conductors. The dielectric layer between them is affected by wetness arising from incontinence events. Thus the dielectric layer between the interdigitated members 402a and 402b undergoes permittivity changes during wetness events, thereby influencing the capacitance value and hence the resonance characteristics of the sensing element 400.

As mentioned above, ideally the sensing elements of the sensor device have minimal adverse effect on the absorbent behavior of the pads with which they are used. It has been mentioned that the conductive members of the capacitors incorporated into the sensing elements may be water permeable and this may be achieved in a number of ways. FIG. 10a shows an example of a conductive member 1002 in the form of a capacitive plate which has been formed on a substrate layer 1004 e.g. using printing, bonding or other deposition process. Holes or channels 1030 have been formed for flow of wetness across the member 1002. Here, holes in the conductive member 1002 have slightly larger diameter than the holes in substrate layer 1004.

While FIGS. 7a and 7b shows a planar capacitor C having interdigitated fingers, it is to be understood that typical parallel plate capacitors may be used. Where interdigitated capacitor fingers are employed, the capacitor element may run along an extended length of the sensor device, e.g. to cover a large area of the absorbent article into which the sensor device is incorporated. This is exemplified in the schematic drawing of FIG. 8a which shows another single element resonant capacitor sensing element.

Here, sensing element 400 extends along a length of an absorbent article 850 and is in communication with an inductive component 404 (secondary coil behaving as a transmitter) toward one end of the article. The sensing element 400 is coupled, via induction, with a primary coil 204 (shown in broken lines) inside clamp 200 which contains or is attached to or further coupled with a receiver device (not shown).

FIGS. 10b, 10c and 10d show interdigitated capacitors with first conductive member 1012, second conductive member 1022 and substrate layer 1004 there between. In FIG. 10b flow channels in the form of holes 1050 are provided in the conductive members 1012, 1022 and the substrate layer 1004 that they are printed onto. In FIG. 10c, the holes 1030 are formed in the substrate layer 1004, but not the conductive members of the capacitor so as to avoid direct exposure of the conductive members to moisture. In FIG. 10d, the holes are larger slots, formed in the substrate layer 1004. Larger slots have been found to enable moisture in the pad to wick away from the sensor elements and into the absorbent layers of the pad effectively. The conductive elements shown in each of FIGS. 10a to 10d may be manufactured in bulk (e.g. by printing a conductive coating or interdigitated tracks onto each side of a substrate), and then punching, etching, drilling, cutting or otherwise forming holes or slots, slits or channels in the substrate and/or the conductive members. Large sheets may then be cut to size for use as individual sensing elements in absorbent articles. In one embodiment, the substrate is 0.15 mm polyimide. The shapes of the holes, slits or channels are ideally determined to maximize absorption of liquid into the absorbent layers of the pad and away from the skin and to minimize the flow of liquid back from the absorbent core toward the subject, when the absorbent article is subject to pressure from the subject sitting or moving.

In another arrangement, interdigitated capacitive fingers may be charged alternatively so that there is a dielectric (and hence capacitance) between adjacent fingers of the same conductive member, as well as between fingers of opposing conductive members. This arrangement may provide for directional sensing of wetness events and may enable differential sensing of wetness that moves from inner to outer layers of the absorbent articles or vice versa. This has usefulness in distinguishing 'original' wetness events from false events that are caused by back wetting (liquid stored in outer layers being forced back toward the subject due to e.g. movement or overfilling of the pad).

In another arrangement, the conductive members may be bonded, laminated, covered, coated with or made from a material which is minimally hydrophobic on its underside (distal the subject's skin) to maximize wicking of liquid away from the sensing elements. This material may comprise a material already used in the construction of the absorbent article for example in the ADL (Acquisition and Distribution Layer).

Alternatively/additionally, the conductive elements may be bonded, laminated, covered or coated with a material which is minimally hydrophobic on its upper side (proximal the subject's skin) to minimize the amount of liquid remaining on the upper surface of the conductive member and maximize the drawing of liquid into holes, slits or channels in the member. Alternatively/additionally, such a material may be bonded and/or laminated with or into the cover stock of the absorbent article to prevent or minimize trapping of liquid in the layers of the absorbent article which are closest to the subject's skin, and to maximize the drawing of liquid into holes, slits or channels formed in the conductive members.

One or more further layers may also be incorporated between the conductive members and the core of the absorbent article to prevent or minimize the flow of liquid back up from the absorbent core and toward the conductive members of the sensor device. This minimizes the risk of erroneous wetness detection caused e.g. as a result of a redistribution of pressure (and ejection of liquid from within the absorbent article) during use. This is occasionally referred to as "back wetting".

In some embodiments, part or all of the area of a conducting member which may come into contact with wetness during use may have one or more wetness flow control features which may enhance performance of the sensor. The features may apply to the conducting member itself, or to a material layer applied either directly or indirectly to the conducting member which has features that influence the spread of moisture over the conducting member. In one embodiment, illustrated in FIGS. 11 and 11a, the flow control features are surface features in the form of a grid formed in a hydrophilic material layer 700 applied or bonded with adhesive 710, to the conducting member 720.

The hydrophilic material layer 700 will normally be a light weight material, typically tens to low hundreds of grams per square meter, and may comprise one or more of a wide range of absorbent materials such as a nonwoven fabric comprising a hydraulically entangled blend of cellulose and polyester fibers. The bonding agent 710 that attaches the hydrophilic material layer 700 to the conducting member 720 may be selected from a range of adhesive materials that are typically tens of micrometers in thickness and have substantially no or minimal effect on the performance of the conducting member.

The grid may be etched, inscribed, scored, shaped, moulded, stamped or otherwise formed in the material layer 700 or the conducting member 720 in such a way that each grid element (cell) 700a is bounded by an absence or reduction in hydrophilic material. The geometric design of the grid will depend on the underlying sensor design, however it will typically be a quadrilateral structure, typically with rectangular elements of length L and width W that are millimeters or low tens of millimeters, and with a controlled gap of low millimeters or fractions of millimeters between each grid element being a gap X adjacent to the length of the grid element and a gap Y adjacent to the width of the grid element for rectangular structures. See, for example, FIG. 11a which shows an expanded view of Section A from FIG. 11.

Alternatively the flow control features may be chemical rather than geometrical, and formed by reducing hydrophilic performance of the material layer or conducting member at the cell boundaries e.g. by controlling the charge or hydroaffinity of the material/member. In use, the cell boundaries (whether physical or chemical) behave as capillary barriers which confine wetness to a "cell" of the grid, until there is sufficient liquid to cross a boundary and start filling of an adjacent cell. This helps to maintain the sensitivity of the sensor for longer periods of use.

In an alternative arrangement, a plurality of sensing elements, each comprised of a resonance circuit such as the kind utilizing interdigitated finger capacitors, may be incorporated into an absorbent article, together forming the sensor device.

The plurality of sensing elements may be spaced apart within the absorbent article or on a surface (e.g. inner or outer) surface of the absorbent article while worn. Spacing apart may be from front to rear of the article or from side to side, e.g. in the leg area where risk of wetness and wetness leakage may be higher. Alternatively/additionally, sensing elements may be distributed at different depths of the absorbent layer so that a processor processing signals from the sensor device can provide depth resolution as well as or as an alternative to area resolution which may indicate spread of wetness along the article.

In one embodiment, a first sensing element provided on or toward an outer layer of the absorbent article i.e. the layer most distal from the subject, and a second sensing element is placed on or toward the surface contacting the subject's skin. This enables the sensor device to detect the presence of wetness in 2 different layers of the absorbent article, and enables a processor processing signals obtained from the sensing elements to interpolate what is occurring within the layers of the absorbent article. In such an embodiment, the first sensing element has a slower response to a wetness event because of the time taken for the liquid to be drawn into the absorbent material but provide a relatively stable response signal. This can be detected by the processing means monitoring the time and nature of the change in resonance characteristic exhibited by that sensing element. In contrast, the second sensing element responds faster because of its closer proximity to the wetness in the pad and so may be capable of indicating the type of event (e.g. urinary or faecal). The second sensing element may also be more responsive to the onset of multiple wetness events, whereas the first sensing element has greater reliability for detecting cumulative void volumes. Depending on the geometry of the sensing elements, they may also be used to sense wetness at different layers of the absorbent article and so, enable improved volumetric estimates by a processor processing signals from the discrete sensing elements.

In one embodiment, the processing means (e.g. in a body worn receiver device or a remote station) processing signals derived from the sensing elements is able to integrate the response over the distance between the first and second sensing elements to estimate the volume of wetness in the wetness event.

The multiple sensing elements may communicate with a receiver by one or more inductive transmitter coils at one end of the absorbent article which in turn can be inductively coupled with a corresponding inductive coil (receiver) inside the clamp 200. This is akin to the contactless coupling arrangement of inductive component 404 and clamp 200 in FIG. 8*a*. In an embodiment, the receiver is in communication (either directly or indirectly) with a processor performing e.g. Fast Fourier Transform (FFT) processing on the received data to determine the change in resonance behavior for each circuit. As described in the above, the multiple sensing elements may, alternatively, communicate with a receiver via a RF chip provided in the absorbent pad and in communication with the sensing elements.

Ideally, the capacitive and inductive components within each sensing element are planar in construction. This is advantageous because the impact of movement of the subject on their characteristic performance is small compared to corresponding sensing elements which span different depths of the absorbent article such as, for example, the more traditional capacitive sensing elements of FIGS. 1 to 4. Thus, an interdigitated capacitor with arm or finger members sitting in a plane in a layer of the absorbent article enable the sensing element to flex during movement of the subject giving rise to significantly reduced impact on sensor signals arising from use of the sensing element.

In a preferred embodiment, and as alluded above, the sensor device includes a plurality of sensing elements distributed throughout an absorbent article to provide spatial resolution (area and/or depth) for wetness detected using the device (see for example FIG. 8*b*). Individual sensing elements ideally incorporate a resonance circuit e.g. of the kinds illustrated in FIGS. 7*a* and 7*b*. FIG. 7*a* shows the planar inductive component L situated adjacent the planar capacitive component C. The inductive component L may alternatively be formed as a planar coil extending around the capacitive component rather than situated adjacent to it, as illustrated in FIG. 7*b*. Other examples are shown in FIGS. 10*a* to 10*d*.

Preferably, each of the sensing elements in or on the absorbent article is encapsulated or coated in a waterproof or liquid impermeable material. This prevents formation of an electrical circuit between electrically conductive components of the sensing elements in the presence of an electrolyte such as water or urine. However, encapsulation is not provided for conductive sensing elements incorporated into the sensor device.

Some of the earlier stated sensor embodiments include designs to compensate for external environmental effects, such as subject movements. It is to be understood that those compensating elements, such as the sealed reference capacitor noted earlier, may be applied to other sensor arrangements discussed herein, including resonant circuits, where the type of sealed reference element, including capacitive, inductive, resistive, or combinations thereof, will depend on the sensor element that has varying electrical behavior attributable to environmental factors such as wetness.

A plurality of sensing elements e.g. of the kind shown in FIGS. 7*a*, 7*b* and 10*a* to 10*d* may be fabricated onto a continuous substrate or intermediate layer which is spooled onto a roll. The substrate may be a liquid permeable polymer, non-woven or woven material, hemp, wadding or other substrate layer suitable for incorporation into the absorbent article. Fabrication may involve printed electronics techniques in which the sensing elements are printed directly onto a substrate layer using conductive ink (e.g. silver), carbon nano-tubes or the like. It is envisaged that utilizing printed electronics on a polymer substrate such as Mylar or Polyimide is likely to produce a sensor which is less likely to fail due to discontinuities in the conductive pattern caused by stretching during fabrication.

FIG. 12 is a schematic illustration of a method for manufacturing an absorbent article with sensing elements, according to embodiments of the present invention.

Fabrication of sensing elements may involve screen printing, gravure or other methods, as may be known to one of skill in the art. These methods are capable of producing resolutions which are adequate for fabrication of the resonance circuits disclosed herein, and can include additional elements such as resistors, fuses and the like as may be designed into the sensing elements from time to time. These methods enable fabrication of planar inductive coils that can be built onto one side of a substrate layer which simplifies the fabrication method. Further, these printing methods can deposit small value capacitors which may be ideal in embodiments of the present invention, and at a throughput of e.g. 60 $m^2$ per second. This is around 600 times faster than traditional photolithography techniques.

Ideally, the layout of the sensing elements is distributed so that there is minimal bulging when the fabricated material is spooled onto a roll. Thus, distribution of the sensing elements may involve alternating lateral displacement of the elements and/or staggering them when fabricated onto the substrate (step 1201), to avoid or minimize stacking of the elements when the substrate is spooled. Spooling (step 1202) may include or be substituted by, e.g. rolling the fabricated substrate onto a spool core, or folding it in a zigzag manner. The roll of substrate having the sensing elements fabricated into it may then be used as feedstock into a typical pad production line e.g. of the kind already used to produce diapers and absorbent pads (step 1203). This requires minimal modification to existing pad manufacturing sites, limiting the capital costs required to retrofit production lines for non-sensing pads to produce pads or other absorbent articles that incorporate a sensing device according to embodiments of the present invention.

Alternatively, the sensing elements may be manufactured individually using printed circuit board techniques (ideally on a flexible substrate) or other techniques and placed into absorbent articles including pads, diapers and the like using a pick and place approach. This may facilitate placement of sensing elements in different layers of the absorbent articles during the production process which provides depth resolution as well as area resolution in the detection of wetness. However, this typically involves use of robotics which requires significant plant investment. This approach may also lead to a reduction in typical pad manufacturing throughput which, for pads not containing sensors is typically 300 to 500 pads per minute.

Robotics employed to manufacture pads incorporating sensing elements may involve use of a vacuum to pick up and place the sensing elements over the various pad layers during reproduction (steps 1204, 1205, 1206). Advantageously, a vacuum placement approach has positioning specificity whilst not requiring physical grasping or gripping of the sensing elements which could scratch or otherwise damage components of those sensing elements. Placement of sensing elements within an absorbent article may be e.g. on a base layer of the article, under a cover stock or over a cover stock used in the article.

In any case, during manufacture of absorbent articles incorporating sensing elements according to embodiments of the invention, it is desirable that the materials are maintained in tension to maintain and control tracking of the production process. When the various layers have been assembled, they can be cut to size. Synchronization and alignment of layers is critical prior to cutting. Cutting may be achieved by use of a blade on a rotating drum (step 1208), where the blade on the drum is positioned to cut the materials to the size required e.g. for an individual absorbent article.

In one embodiment, the cutting drum is servo-driven to a registration mark (step 1207) on the un-cut material to ensure correct placement of the blade prior to cutting. The registration mark may be a visible mark or a mark provided which fluoresces when irradiated e.g. with ultra-violet energy. Alternatively/additionally, the registration mark may be a notch, hole, protrusion or node which is magnetically or electronically detectable, and/or may utilize the resonance of individual sensing elements incorporated on or into the absorbent layers. In one embodiment, a registration mark is provided as a guide for location of a receiver device being attached to the absorbent article. In one arrangement the registration mark may provide tactile or physical coupling cues, e.g. by providing one or more holes that are alignable with one or more protrusions in the receiver before it is clamped onto the absorbent article. These tactile or physical cues may help users to correctly align the inductive coils in the receiver and absorbent article during use.

An example of an absorbent article incorporating three sensor elements is illustrated in FIG. 8b. Ideally, these sensing elements are resonance circuits. When the sensor device contains multiple connected sensing elements in the form of resonance circuits, it is desirable that each sensing element has a known characteristic resonance behavior which enables the receiver to determine which of the sensing elements is experiencing a change brought about by wetness. In one embodiment, each sensing element has a characteristic resonance frequency that is separately identifiable. In one embodiment, the resonance frequency of each element in the device is ideally separated by at least the sweep frequency range employed by the signal source 600.

In the embodiment illustrated in FIG. 8b, there is contactless coupling between the sensing elements 802 and a receiver device 300. This is achieved by use of a primary inductor coil 990 provided in an antenna layer 900 which is worn over the absorbent article 850. The antenna layer 900 may be provided on or in a flexible substrate layer 980 with the antenna 990 provided in the form of an inductive coil having a number of windings necessary for coupling of energy between the receiver device 300 and the sensing elements 802. The substrate layer 980 may be held in place by an adhesive or other suitable means. The substrate layer may have an adhesive backing for application to an external surface of the absorbent article 850. Alternatively, an adhesive may be applied to an external surface of the absorbent article (ideally on its outer-most surface when worn) for fixedly receiving the antenna layer 900.

In one embodiment, the antenna layer 900 may be provided on or in a garment such as overpants worn by the subject to hold the absorbent article 850 in place during wearing. In either case, the inductive coil 990 may be manufactured into the antenna layer by any suitable means. This may involve use of conductive thread stitched into the material of the overpant or substrate layer, and/or using conductive ink or glue printed onto the overpant/substrate, or using other means as may be known in the art.

The inductive coil 990 in antenna layer 900 acts as a primary coil to pick up resonance signals emitted from each of the sensing elements 802. The antenna layer 900 has coupling points 910 for physical electrical connection with corresponding coupling points in a receiver device 300 with which the sensor device is used, although other forms of coupling between the antenna layer and the receiver device are contemplated. Also contemplated is an embodiment having the receiver integrated into the antenna layer or overpant.

In the embodiment illustrated in FIG. 8b sensing elements 802 combined with inductive coil 990 and coupling points 910 together form a sensing device, according to an embodiment of the invention, for use with a receiver, for sensing wetness in an absorbent article 850 arising from incontinence events. In this embodiment, the individual sensing elements 802 enjoy contactless coupling with the receiver (not shown) by taking advantage of the inductance in each sensing element (comprised of a resonance circuit) which acts as a secondary coil for contactless coupling with inductive coil 990 in the antenna layer 900.

The coupling points 910 on antenna layer 900 may be e.g. press studs or other metallic/conducting terminating points 310 which enable quick and easy attachment to a corresponding coupling member in the receiver device 300. The corresponding coupling member 310 on the receiver device 300 provides complimentary press stud or other contacts to secure electrical contact between the receiver device 300 and the inductive coil 990. Alternatively, clips, clamps and traditional socket connectors (akin as those used in computing and audiovisual components) may be utilized as would be understood by one skilled in the art.

In any event, contact coupling between the antenna layer 900 and the receiver device 300 should be easy to use and reliable so that connection and disconnection can be performed quickly, with minimal mental and physical exertion, minimal visual inspection and little cause for frustration, whilst maintaining a robust and reliable electrical connection while connected. Whereas the embodiment in FIG. 8a requires alignment between the inductor associated with the sensing element and the inductor within the receiver device while energy is transferred between the two, use of the inductive coil 990 in FIG. 8b eliminates the need for careful alignment. Instead, the receiver device 300 is clipped onto the antenna layer 900 at the coupling point 910 which is very easy for nurses, carers and incontinent subjects themselves to achieve.

Use of resonance circuits in the sensing elements of the present invention is power efficient because the elements operate at a resonance frequency at which power consumption is minimized. Where a swept frequency is used to interrogate the resonance circuits employed in the sensing elements, the sweep rate can be controlled to balance power requirements against measurement accuracy and timeliness of detection.

Further use of resonance circuits in the sensing elements enables detection of wetness by monitoring changes in e.g. resonance frequency which is typically more accurate than sensing changes in amplitude, as in the case with existing incontinence sensors that rely on changes in resistance in a simple conductive wetness sensor. Further, in embodiments where there is no electrical contact between the signal source and the sensing elements (i.e. where there is contactless coupling), the device has minimal compliance issues with standards such as e.g. IEC 60601.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components or group thereof.

It is to be understood that various modifications, additions and/or alterations may be made to the parts previously described without departing from the ambit of the present invention as defined in the claims appended hereto.

The invention claimed is:

1. A sensor device for detecting a wetness in an absorbent article worn by a subject, the sensor device including:
   (a) one or more capacitive sensing elements formed by first conductive member and a second conductive member separated by a dielectric region; and
   (b) a coupling for communicating sensor signals between the one or more sensing elements and a receiver;
      wherein a change in wetness caused by a wetness event in the absorbent article causes a change in capacitance for at least one of the sensing elements, which change in capacitance is detectable to determine occurrence of a wetness event in the absorbent article, and wherein the changes in capacitance are communicated in the sensor signals to the receiver; and
      wherein at least one of the one or more capacitive sensing elements includes a third conductive member and wherein a change in capacitance between first and second conductive members of the at least one capacitive sensing element is detectable relative to a change in capacitance between one of (i) the second and third conductive members, and (ii) the first and third conductive members.

2. A sensor device according to claim 1 including one or more spacers for substantially maintaining a known distance between at least the first and second conductive members.

3. A sensor device according to claim 1, wherein one of the conductive members is a base layer of the absorbent article, and the dielectric region includes a fill layer of the absorbent article.

4. A sensor device according to claim 1, including a further conductive member which forms a reference capacitor with either of the first and second conductive members without altering the capacitor formed by the first and second conductive members, wherein the reference capacitor is sealed from wetness, and wherein the reference capacitor provides an indicator of an impact of non-wetness related external factors on the performance of the capacitor formed by the first and second conductive members.

5. A sensor device according to claim 1, wherein the change in capacitance is detectable by measuring a change in one or more of:
   (a) resonance frequency of a sensing element;
   (b) Q-factor of a sensing element;
   (c) current drawn from the primary circuit;
   (d) impedance in the sensing element;
   (e) amplitude of a reflection signal from the secondary circuit;
   (f) magnetic field strength;
   (g) electric field strength; and
   (h) patterns of any of (a) to (g) observable in time and/or frequency.

6. A sensor device according to claim 5, wherein two or more sensing elements among the one or more sensing elements are spaced apart, each of the spaced apart sensing elements having a different characteristic resonance behaviour.

7. A sensor device according to claim 6, wherein the spaced apart sensing elements are arranged in a substantially planar arrangement relative to the absorbent article.

8. A sensor device according to claim 6, wherein the spaced apart sensing elements are arranged at different depths of the absorbent article.

9. A sensor device according to claim 1, wherein at least one of the sensing elements includes plurality of interdigitated capacitive fingers.

10. A sensor device according to claim 1, wherein at least one sensing element of the one or more sensing elements is substantially planar.

11. A sensor device according to claim 1, wherein the one or more sensing elements include conductive members of at least one capacitive sensing element which are isolated from moisture in the absorbent article.

12. A sensor device according to claim 1, including a plurality of pores or channels permitting movement of moisture across the sensing elements and into the absorbent article.

13. A sensor device according claim 1, including one or more flow control features which encourage discretised spread of moisture over a surface of a conducting member in at least one of the one or more sensing elements.

14. A sensor device according to claim 13, wherein the one or more flow control features are selected from a group including:

(a) surface features in a cover layer over the conducting member, or in the conducting member itself, which define boundaries across which liquid less readily flows; and (b) chemical or charged features in a cover layer over the conducting member, or in the conducting member itself, which define boundaries across which liquid less readily flows.

15. A sensor device according to claim 13, wherein the flow control features are arranged to form a grid over the conducting member.

16. A sensor device according to claim 1, further including a compensating reference element that is:
   (a) isolated against a parameter that is being measured; and
   (b) susceptible to external environmental factors in a manner similar to the one or more sensing elements;
      wherein the reference element provides an indicator of the impact of the external environmental factors on the performance of the sensing element.

17. A sensor device according to claim 1, wherein the coupling includes a contact coupling between at least one of the one or more sensing elements and the receiver.

18. A sensor device according to claim 1, wherein the coupling includes a contactless coupling between at least one of the one or more sensing elements and the receiver.

19. A sensor device according to claim 18, wherein the contactless coupling is a magnetic/inductive coupling.

20. A sensor device according to claim 19 wherein the contactless coupling includes an inductive component being a coil formed around and substantially planar with a connected capacitive component of at least one of the one or more sensing elements.

21. A sensor device according to claim 19 wherein the contactless coupling includes an inductive component being a coil formed adjacent to and substantially planar with a connected capacitive component of at least one of the one or more sensing elements.

22. A sensor device according to claim 19 wherein the contactless coupling includes an inductive component formed on or into an antenna attachment that is separate from the absorbent article.

23. A sensor device according to claim 22 wherein the antenna attachment is placed over a surface of the absorbent article and held in place with an adhesive.

24. A sensor device according to claim 22 wherein the antenna attachment is incorporated into a garment worn with the absorbent article by the subject.

25. A sensor device according to claim 22, wherein the antenna attachment includes a contact coupling for electrical connection with a receiver.

26. A sensor device according to claim 1, fabricated into a flexible insert attachable to an absorbent article or other garment worn by a subject.

27. An absorbent article incorporating a sensor device according to claim 1.

28. An absorbent article incorporating a sensor device according to claim 1 and further including a resistive component with each of the one or more sensing elements.

29. An absorbent article incorporating a sensor device according to claim 28 wherein the resistive component is a thermistor.

30. A method for manufacturing an absorbent article incorporating a sensor device according to claim 1, the method including the steps of:
   fabricating a continuous length of material having a plurality of spaced apart sensing elements each comprising the first conductive member, the second conductive member, the third conductive member and the coupling;
   spooling the fabricated material onto a roll; and
   incorporating the spooled material into the inline feedstock of a production facility producing absorbent articles.

31. A method according to claim 30 including arranging the one or more capacitive sensing elements so they are spaced apart in a pattern which reduces stacking of one or more capacitive sensing elements or parts thereof when the material is spooled onto the roll.

32. A method for fabricating an absorbent article incorporating a sensor device according to claim 1, the method including:
   operating a placement device to generate a vacuum for releasably collecting ones of the one or more sensing elements;
   placing the collected ones of said one or more sensing elements in a desired location on a layer of material of the absorbent article; and
   releasing the ones of said one or more sensing elements onto the material to form fabricated material for producing the absorbent article.

33. A method according to claim 32 further including the step of applying an adhesive to one of the sensing element and the material before the releasing step.

34. A method according to claim 30, including the step of utilising a registration mark on the fabricated material to place a cutting blade prior to using the blade to cut the fabricated material to size.

35. A method according to claim 30, including rotating a drum having a cutting blade to cut the fabricated material.

36. A method according to claim 30, including the steps of:
   (a) cutting the fabricated material into lengths suitable for incorporation into the absorbent article;
   (b) placing a length of the fabricated material onto a layer of the absorbent article in fabrication; and
   (c) assembling remaining layers of the absorbent article.

37. A method according claim 30, wherein the lengths of fabricated material are cut by rotating a drum having one or more cutting blades thereon, wherein rotation of the drum during cutting is controlled with respect to a registration mark on the fabricated material, for positioning at least one of the blades.

38. A method according to claim 30, including the step of transferring one or more cut lengths of the fabricated material using a negative pressure/vacuum source, positioning the cut portions onto a layer of the absorbent article, and releasing the cut portion from the negative pressure/vacuum source.

39. A method according to claim 30, including the step of incorporating in the fabricated material one or more identifiers comprising one or more of:
   (a) a designated cutting zone;
   (b) a connection zone for a contactless coupling;
   (c) a location of a sensing element within the absorbent article;
   (d) a batch number of the sensing elements; and
   (e) a performance rating of a sensing element.

40. A method according to claim 30, including the step of incorporating in the fabricated material a registration mark selected from the group including one or more of a notch, hole, protrusion, metallic node, magnetic node, fluorescent marker and a visible marker.

41. A sensor device according to claim 1 wherein the coupling includes an antenna attachment for transmission of energy between the one or more sensing elements of the sensor device and a signal source, the antenna attachment including:

a substrate;

an antenna coupling for coupling the antenna attachment with a signal source for current flow there between; and an inductive coil fabricated on or into the substrate, the coil having sufficient turns for inductive energy transfer between the one or more sensing elements and the inductive coil.

42. A sensor device according to claim 41, wherein the substrate is a flexible layer formed from a material selected from the group including, but not limited to: a polymer, a non-woven material, a woven material, paper and hemp.

43. A sensor device according to claim 41, wherein the substrate comprises a garment worn by a subject.

44. A sensor device according to claim 43, wherein the garment is an overpant worn by a subject.

45. A sensor device according to claim 41, wherein the substrate comprises a napkin which is removably attachable to an external surface of an absorbent article worn by the subject.

46. A sensor device according to claim 41, attachable to an absorbent article by means of adhesive gum provided on one of the substrate of the antenna attachment and the absorbent article.

47. A sensor device according to claim 41, wherein the inductive coil is fabricated using one or more of a conductive thread or ribbon woven or stitched into the substrate.

48. A sensor device according to claim 41, wherein the inductive coil is fabricated onto the substrate using one or more of a printed conductive ink, conductive thread, ribbon or the like.

49. A sensor device according to claim 41, wherein the antenna attachment is reusable.

50. A sensor device according to claim 41, wherein the inductive coil is configured for solid core based coupling with a signal source containing a corresponding inductive coil.

51. A method for manufacturing an absorbent article incorporating a sensor device, the method according to claim 30 and including the steps of folding the fabricated continuous length of material in a zigzag manner into a heap, and incorporating the heap of folded material into the inline feedstock of a production facility producing absorbent articles.

52. A sensor device according to claim 1, wherein at least one of the one or more sensing elements includes interdigitated capacitive fingers charged alternatively so that there is a dielectric and hence capacitance between adjacent fingers of the same conductive member, as well as between fingers of opposing conductive members.

\* \* \* \* \*